(12) United States Patent
Livak et al.

(10) Patent No.: US 6,884,583 B2
(45) Date of Patent: Apr. 26, 2005

(54) DETERMINATION OF A GENOTYPE OF AN AMPLIFICATION PRODUCT AT MULTIPLE ALLELIC SITES

(75) Inventors: Kenneth J. Livak, San Jose, CA (US); Federico Goodsaid, San Jose, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 10/104,774

(22) Filed: Mar. 21, 2002

(65) Prior Publication Data

US 2002/0164630 A1 Nov. 7, 2002

Related U.S. Application Data

(63) Continuation of application No. 09/018,595, filed on Feb. 4, 1998.

(51) Int. Cl.[7] .................. C12Q 1/68; C12P 19/34; C07H 21/02
(52) U.S. Cl. .............. 435/6; 435/91.2; 435/91.5; 536/22.1; 536/23.1; 536/24.3; 536/24.31; 536/24.32; 536/24.33
(58) Field of Search .................. 455/6, 91.1, 91.2; 536/23.1, 24.3

(56) References Cited

U.S. PATENT DOCUMENTS

| | | | |
|---|---|---|---|
| 5,075,216 A | 12/1991 | Innis et al. ............. | 435/6 |
| 5,210,015 A | 5/1993 | Gelfand et al. ........... | 435/6 |
| 5,418,149 A | 5/1995 | Gelfand et al. ........... | 435/91.2 |
| 5,538,848 A | * 7/1996 | Livak et al. ............. | 435/5 |
| 5,723,591 A | 3/1998 | Livak et al. | |
| 5,736,333 A | * 4/1998 | Livak et al. ............. | 435/6 |
| 5,759,781 A | 6/1998 | Ward et al. ............. | 435/6 |
| 5,763,181 A | 6/1998 | Han et al. ............. | 435/6 |
| 5,792,610 A | 8/1998 | Witney et al. ........... | 435/6 |
| 5,834,181 A | 11/1998 | Shuber ............... | 435/5 |
| 5,876,930 A | 3/1999 | Livak et al. | |
| 6,015,667 A | * 1/2000 | Sharaf ............... | 435/6 |
| 6,030,787 A | 2/2000 | Livak et al. | |
| 6,150,097 A | * 11/2000 | Tyagi et al. ............ | 435/6 |
| 6,258,569 B1 | 7/2001 | Livak et al. | |

FOREIGN PATENT DOCUMENTS

| | | | | |
|---|---|---|---|---|
| WO | WO 92/02638 | 2/1992 | ............ | C12Q/1/68 |
| WO | WO 96/15270 | 5/1996 | | |
| WO | WO 97/39008 | 10/1997 | ........... | C07H/21/04 |
| WO | WO 97/46708 | 12/1997 | ............ | C12Q/1/68 |

OTHER PUBLICATIONS

Fortina et al, "Non radioactive detection of the most common mutations in the cystic fibrosis transmembrane conductance regulator gene by multiplex allele specific polymerase chain reaction", Hum Genet. (1992) 90:375–378.*
Woudenberg, T.M. et al., "Quantitive PCR By Real Time Detection", Proceedings of the SPIE; vol. 2680, Jan. 1, 1996; pp. 306–315.

Lee, L.G. et al., "Allelic Discrimination BZ Nick–Translation PCR With Fluorogenic Probes", Nucleic Acids Research; vol. 21, No. 16; Aug. 11, 1993; pp. 3761–3766.
Gibson, U.E.M. et al., "A Novel Method For Real Time Quantitative RT–PCR" Genome Research; vol. 6, No. 10; Oct. 1, 1996; pp. 995–1001.
Livak, et al., "Towards Fully Automated Genome–Wide Polymorphism Screening"; Nature Genetics; vol. 9, Apr. 1995; pp. 341–342.
Rusch, T. et al., "Scanning fluorescence detector for high–throughput DNA genotyping", *SPIE*, vol. 2680, Sep. 1996, pp. 316–325.
Nickerson, D. et al., "Polyphred: automating the detection and genotyping of single nucleotide substitutions using fluorescence based resequencing", *Nucleic Acids Research*, vol. 25, No. 14, pp. 2745–2751.
Tyag, et al., Nature Biotech, 14: 303–308, Mar. 1996.
Faas et al., "Sequence specific priming and exonuclease released fluorescense detection of HLA–DQB1 alleles", Tissue Antigens, vol. 48, (1996), pp. 97–112.
Luedeck, et al., "Fluorotyping of HLA–C: differential detecting of amplicons by sequence specific priming and fluorgenic probein", Tissue Antigens, vol. 50, Dec. 1997, pp. 627–638.
Livak, et al., "Towards fully automated genome–wide polymorphism screening", Nature Genetics, vol. 9, Apr. 1995, pp. 341–342.
Rudert, W. et. al., "Double–Labeled Fluroescent Probes for 5' Nuclease Assays; Purification and Performance Evaluation", BioTechniques, vol. 22, Jun. 1997, pp. 1140–1145.

* cited by examiner

*Primary Examiner*—Jeffrey Fredman
(74) *Attorney, Agent, or Firm*—David J. Weitz; Vincent M. Powers; William D. Schmidt-Kalow & Springut LLP

(57) ABSTRACT

A method is provided for genotyping a target sequence at at least two allelic sites by a 5' nuclease amplification reaction. In one embodiment, the method includes performing a nucleic acid amplification on a target sequence having at least two different allelic sites using a nucleic acid polymerase having 5'→3' nuclease activity and a primer capable of hybridizing to the target sequence in the presence of two or more sets of allelic oligonucleotide probes wherein:

each set of allelic oligonucleotide probes is for detecting a different allelic site of the target sequence, each set of allelic oligonucleotide probes includes two or more probes which are complementary to different allelic variants at the allelic site being detected by the set of probes, the allelic site being 5' relative to a sequence to which the primer hybridizes to the target sequence, and at least all but one of the allelic oligonucleotide probes include a different fluorescer than the other probes and a quencher postioned on the probe to quench the fluorescence of the fluorescer;

detecting a fluorescence spectrum of the amplification;

calculating a fluorescence contribution of each fluorescer to the fluorescence spectrum; and determining a presence or absence of the different allelic variants at the two or more different allelic sites based on the fluorescence contribution of each fluorescer to the combined fluorescence spectrum.

22 Claims, 17 Drawing Sheets

↑ FAM      =   Homozygous for Allele A

↑ TET      =   Homozygous for Allele B

↑ FAM + TET = Heterozygous for Allele A + B

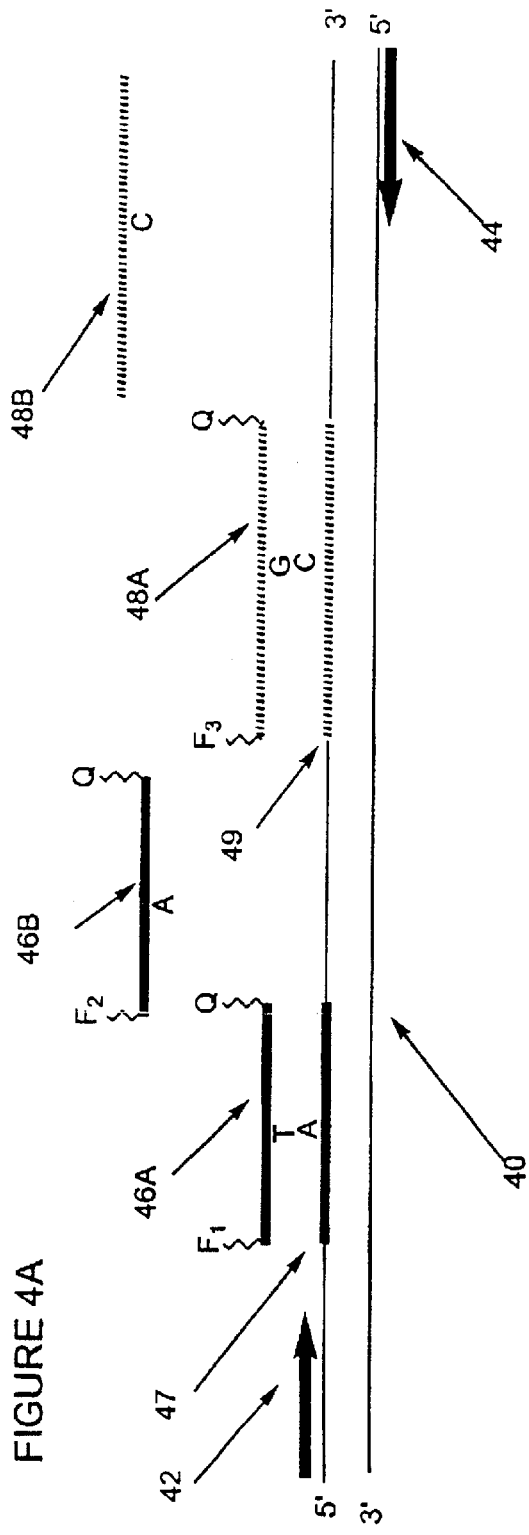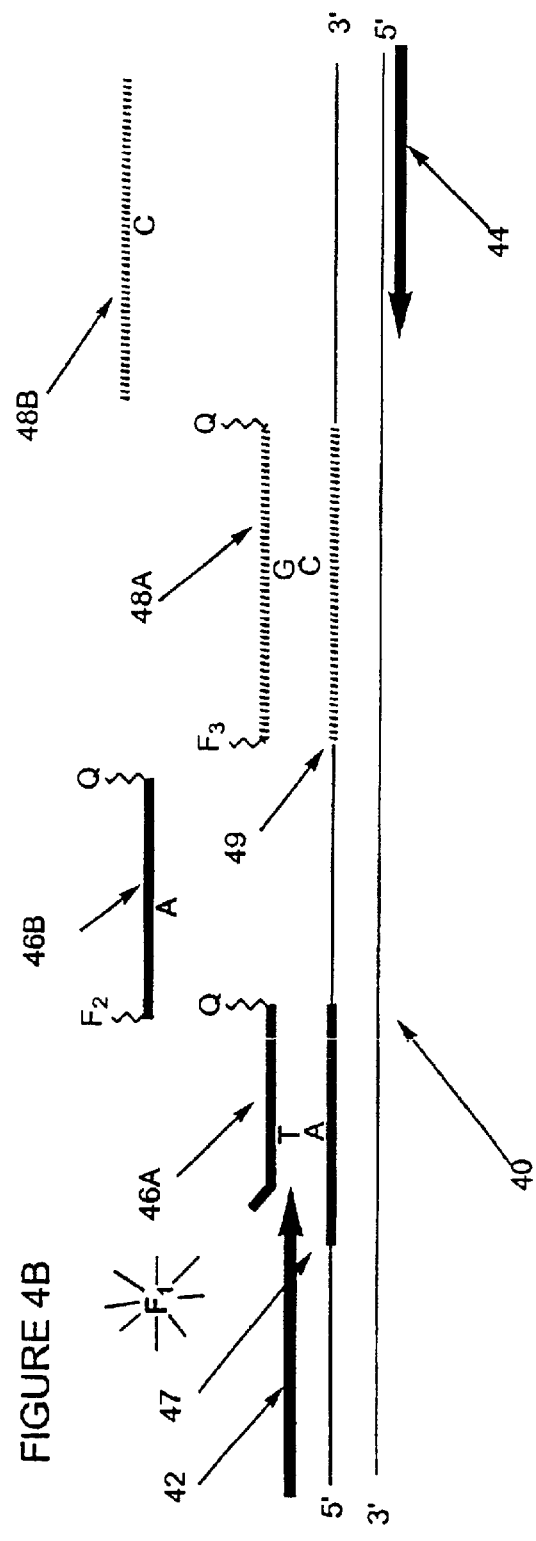

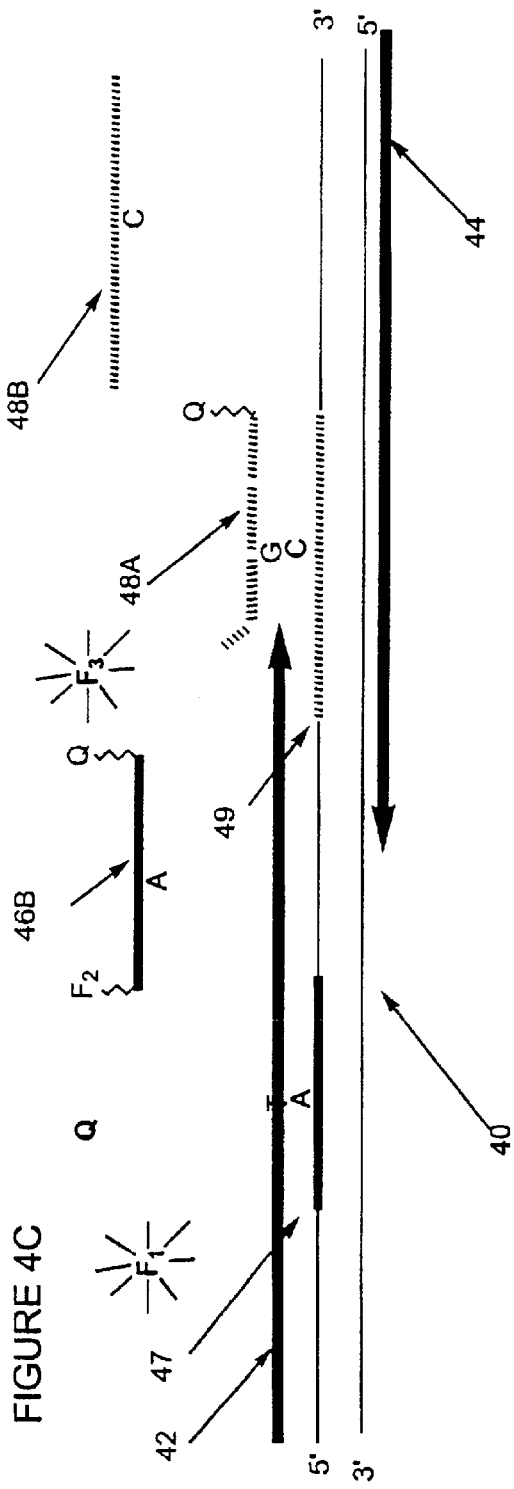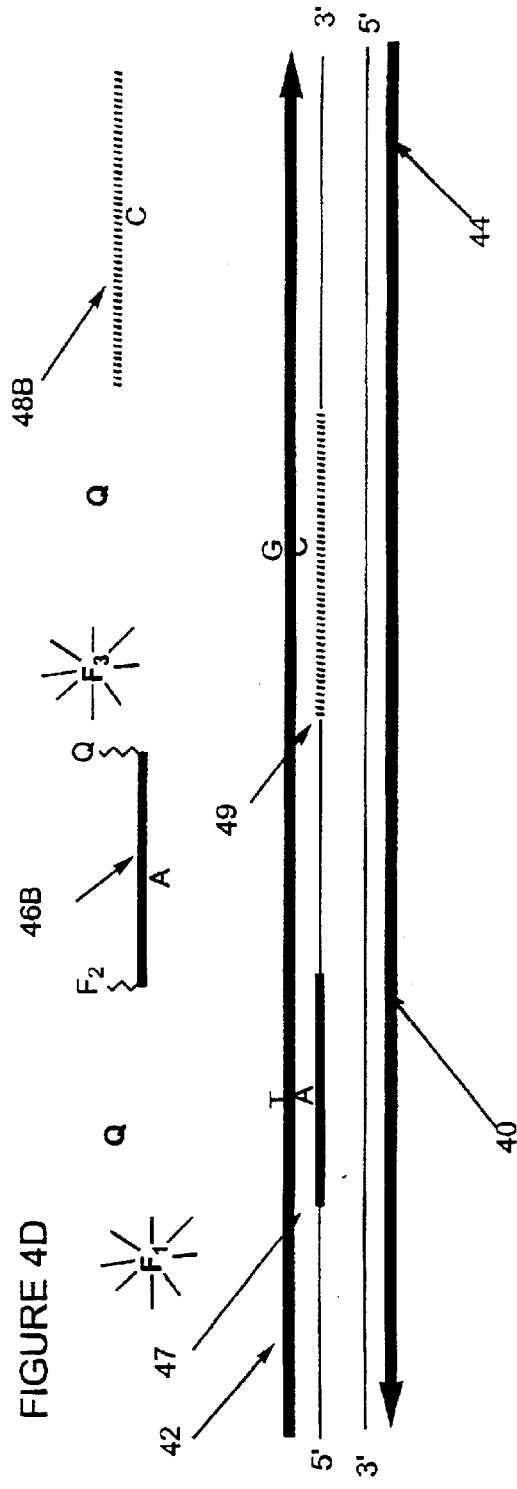

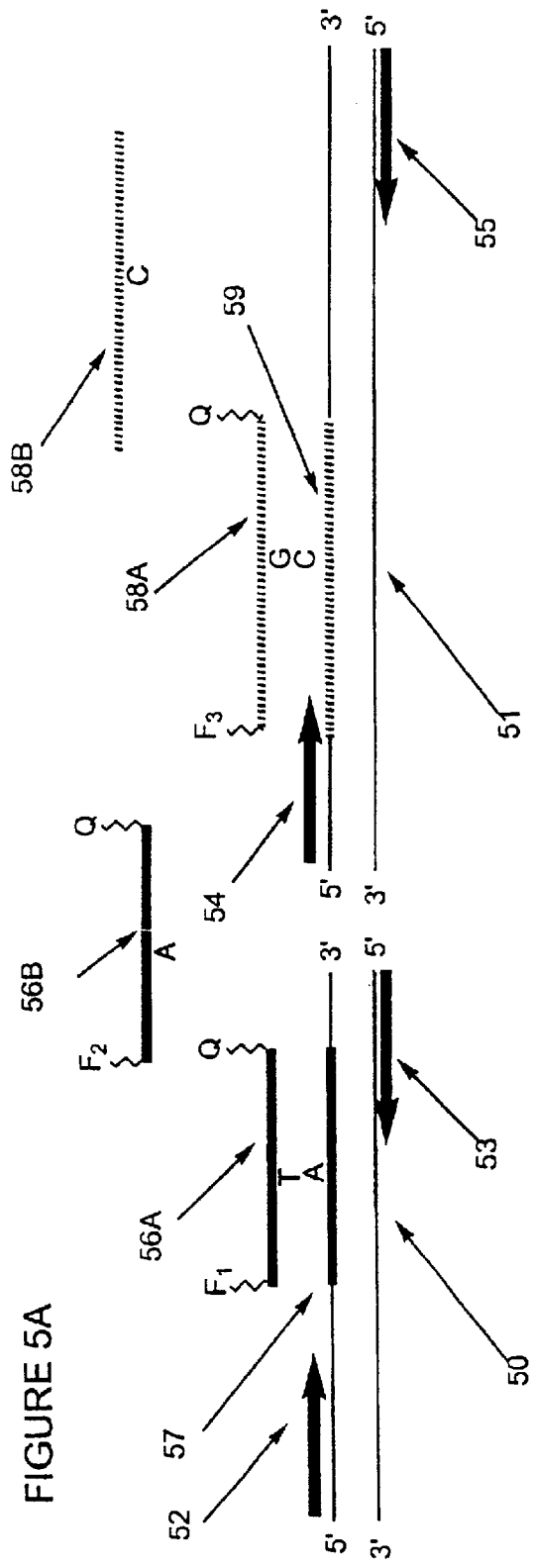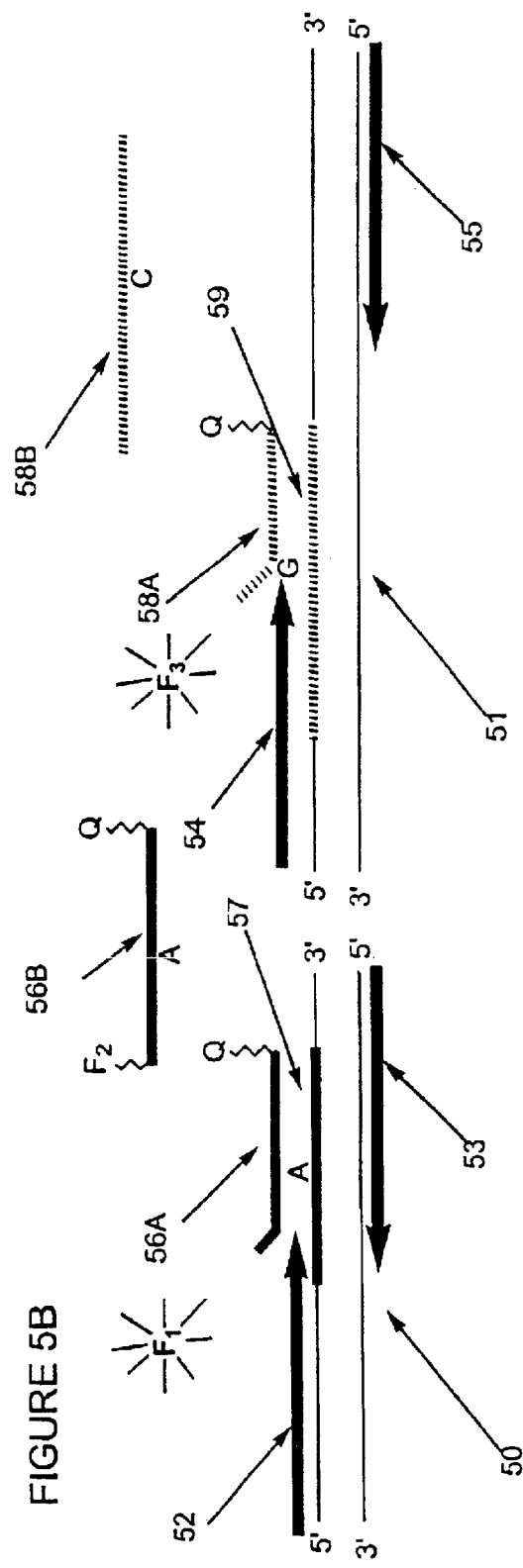

FIGURE 6A

```
CCAGAGGGCAA AA TGCCCTGT AGGTCAATG GG TTTTTTT GCCATCTGAC       50
GGTCTCCGTT TTACGGGACA TCCAAGTTAC CCTAAAAAAA CGGTAGACTG
         └─66

CGTTCTGTCT ATCGTCAGAA GAGGAGACCC CGAAAGAAAG CCTCACagag      100
GCAAGACAGA TAGCAGTCTT CTCCTCTGGG GCTTTCTTTC GGAGTGtctc
                     └─64                  └─64' gctgaagtgg cnacagagaa ggAAGGAGAA GACGGGGACC AGCCCACCAC      150
cgacttcacc gktgtctctt ccTTCCTTCTT CTGCCCCTGG TCGGGTGGTG
 └─68        └─68'

GCCTCCAAG CCCCTAAAGA CCTCCAGTGA GT                          182
CGGAGGTTC GGGATTTCT CA
      └─66'
```

FIGURE 8A

| | | | | | |
|---|---|---|---|---|---|
| AAAGGATCAA | GCATCCCTGA | GTTTCAAACA | GAAACTTGCA | CTGAATACAT | 50 |
| TCAAAGAACC | ATCAAGAAAT | GGGGACCTGG | ATTTTATTTG | CCTGCCTCCT | 100 |
| GGGAGCAGCT | TTTGCCATGC | CTCTACCACC | TCATCCTGGG | CACCCTGGTT | 150 |
| ATATCAACTT | CAGCTATGAG | GTGCTTACCC | CTTTGAAGTG | GTACCAGAGC | 200 |
| ATAAGGCCAC | CGTACCCTTC | CTATGGTTAC | GAGCCCATGG | GTGGATGGCT | 250 |
| GCACCACCAA | ATCATCCCCG | TGCTGTCCCA | ACAGCACCCC | CCGACTCACA | 300 |
| CCCTGCAGCC | TCATCACCAC | ATCCCAGTGG | TGCCAGCTCA | GCAGCCCGTG | 350 |
| ATCCCCAGC | AACCAATGAT | GCCCGTTCCT | GGCCAACACT | CCATGACTCC | 400 |
| AATCCAACAC | CACCAGCCAA | ACCTCCCTCC | GCCCGCCCAG | CAGCCCTACC | 450 |
| AGCCCCAGCC | TGTTCAGCCA | CAGCCTCACC | AGCCCATGCA | GCCCCAGCCA | 500 |
| CCTGTGCACC | CCATGCAGCC | CCTGCCGCCA | CAGCCACCTC | TGCCTCCGAT | 550 |
| GTTCCCCATG | CAGCCCCTGC | CTCCCATGCT | TCCTGATCTG | ACTCTGGAAG | 600 |
| CTTGGCCATC | AACAGACAAG | ACCAAGCGGG | AGGAAGTGGA | TTAAAAGATC | 650 |
| AGAAGATGAG | AGGGGAATGA | ATACTTCAGA | TGCTTTCAGG | AGTGACACAA | 700 |
| GAACACAATG | ATTTTTGCTT | ATAATCACTT | TACTTAGCAA | ATTCTGTAAC | 750 |
| TAAAAAAGTA | CCATTAGCAG | ACAATAAAAT | GCATTAAAAA | TCA | 793 |

FIGURE 8B

```
AGAGGACCAA GCCTCCCTGT GTAGCACAAA GAAAGTTTCT CTGAATATAT      50
TTAAAGAACC ATCAAGAAAT GGGGACCTGG ATTTTGTTTG CCTGCCTTGT     100
GGGAGCAGCT TTTGCCATGC CTCTACCACC TCATCCTGGG CACCCTGGTT     150
ATATCAACTT CAGCTATGAG GTGCTCACCC CTTTGAAGTG GTACCAGAGC     200
ATGATAAGAC CACCATACTC TTCCTATGGT TACGAGCCCA TGGGTGGATG     250
GCTGCACCAC CAAATCATCC CCGTGGTGTC CCAACAGCAC CCCCTGACTC     300
ACACCCTGCA GTCTCATCAC CACATCCCAG TGGTGCCAGC TCAGCAGCCC     350
AGGGTCCGCC AGCAAGCACT GATGCCTGTT CCTGGCCAGC AATCCATGAC     400
TCCAACCCAA CACCATCAGC CAAACCTCCC TCTGCCTGCC CAGCAGCCCT     450
TCCAGCCCCA GCCTGTTCAG CCACAGCCTC ACCAGCCCAT GCAGCCCCAG     500
CCACCTGTGC AACCCATGCA GCCCCTGCTG CCACAGCCAC CTCTGCCTCC     550
AATGTTCCCC CTGCGGCCCC TGCCCCCCAT ACTTCCTGAT CTGCATCTGG     600
AAGCTTGGCC AGCAACAGAC AAGACCAAGC AGGAGGAAGT GGATTAAAAG     650
ACCAGAATAT GAGACAGGAA CTGAAGTAAA CACTTTAGTT GCTTTCAGGG     700
ATGACACAAG CACACAATGA TTTTTGCTTA CAATCACTTA ACTTAGCAAA     750
TTCTGTAACT AAAAATGTAC CAATAGTAGA CAATAAAATG TTTTAAAAAT     800
CA                                                        802
```

FIGURE 9

```
  3  AGGATCAAGCATCCCTGAGTTTCAAACAGAAACTTGCACTGAATACATTCAAAG
     ||||-||||||||||||||||--||||--||||-|||||||-||-|||--|||-|||
  3  AGGACCAAGCCTCCCTGTGTAGCACAAGAAAGAAAGTTTCTCTGAATATTTAAAG

57  AACCATCAAGAAATGGGGACCTGGATTTTATTTGCCTCCTGGGAGCAGCT
     |||||||||||||||||||||||||||||||--||||||--|||||||||
 57  AACCATCAAGAAATGGGGACCTGGATTTTTGTTTGCCTGCCTTGTGGGAGCAGCT

111  TTTGCCATGCCTCTACCACCCTCATCCTGGGCACCCTGGTTATATCAACTTCAGC
     ||||||||||||||||||||||||||||||||||||||||||||||||||||||
111  TTTGCCATGACCTCTACCACCCTCATCCTGGGCACCCTGGTTATATCAACTTCAGC

165  TATGAAGTGCTTACCCCTTTGAAGTGGTACCAGAGC....ATAAGGCCACCGTAC
     ||||||||||||||-||||||||||||||||||||---|||||||||||-|||
165  TATGAAGTGCTCACCCCTTTGAAGTGGTACCAGAGCATGATAAGACCACCATAC

216  CCTTCCTATGGTTACGAGCCATGGGTGGATGGCTGCACCACCAAATCATCCCC
     -|||||||||||||||||||||||||||-||||-|||||||||||||||||||
219  TCTTCCTATGGTTACGAGCCATGGGTGGATGGCTGCACCACCAAATCATCCCC

270  GTGCTGTCCCAACAGCACCCCCGACTCACACCTGCAGCCTCATCACCACATC
     |||-|||||||||||||||||||-|||||||||||||||||||||||||||||
273  GTGGTGTCCCAACAGCACCCCCGACTCACACCTGCAGTCTCATCAGTCACCACATC

324  CCAGTGGTGCCAGCTCAGCAGCCCAGCAACCAATGATGCCCGTT
     |||||||||||||||||||||||||-|||||||||||||-|||
327  CCAGTGGTGCCAGCTCAGCAGCCCGGGTCCGCCAGCACTGATGCCTGTT
```

FIGURE 10

| AAAGGATCAA | GCATCCCTGA | GTTTCAAACA | GAAACTTGCA | CTGAATACAT | 50 |
|---|---|---|---|---|---|
| TCAAAGAACC | ATCAAGAAAT | GGGGACCTGG | ATTTTATTTG | CCTGCCTCCT | 100 |
| GGGAGCAGCT | TTTGCCATGC | CTCTACCACC | TCATCCTGGG | CACCCTGGTT | 150 |
| ATATCAACTT | CAGCTATGAG | GTGCTTACCC | CTTTGAAGTG | GTACCAGAGC | 200 |
| ATAAGGCCAC | CGTACCCTTC | CTATGGTTAC | GAGCCCATGG | GTGGATGGCT | 250 |
| GCACCACCAA | ATCATCCCCG | TGCTGTCCCA | ACAGCACCCC | CCGACTCACA | 300 |
| CCCTGCAGCC | TCATCACCAC | ATCCAGTGG | TGCCAGCTCA | GCAGCCCGTG | 350 |
| ATCCCCAGC | AACCAATGAT | GCCCGTTCCT | GGCCAACACT | CCATGACTCC | 400 |
| AATCCAACAC | CACCAGCCAA | ACCTCCCTCC | GCCCGCCCAG | CAGCCCTACC | 450 |
| AGCCCCAGCC | TGTTCAGCCA | CAGCCTCACC | AGCCCATGCA | GCCCCAGCCA | 500 |
| CCTGTGCACC | CCATGCAGCC | CCTGCCGCCA | CAGCCACCTC | TGCCTCCGAT | 550 |
| GTTCCCCATG | CAGCCCCTGC | CTCCCATGCT | TCCTGATCTG | ACTCTGGAAG | 600 |
| CTTGGCCATC | AACAGACAAG | ACCAAGCGGG | AGGAAGTGGA | TTAAAAGATC | 650 |
| AGAAGATGAG | AGGGGAATGA | ATACTTCAGA | TGCTTTCAGG | AGTGACACAA | 700 |
| GAACACAATG | ATTTTTGCTT | ATAATCACTT | TACTTAGCAA | ATTCTGTAAC | 750 |

FIGURE 11

```
AAAGGATCAA GCATCCCTGA GTTTCAAACA GAAACTTGCA CTGAATACAT     50
TTTCCTAGTT CGTAGGGACT CAAAGTTTGT CTTTGAACGT GACTTATGTA

TCAAAGAACC ATCAAGAAAT GGGGACCTGG ATTTTATTTG CCTGCCTCCT    100
AGTTTCTTGG TAGTTCTTTA CCCCTGGACC TAAAATAAAC GGACGGAGGA

GGGAGCAGCT TTTGCCATGC CTCTACCACC TCATCCTGGG CACCCTGGTT    150
CCCTCGTCGA AAACGGTACG GAGATGGTGG AGTAGGACCC GTGGGACCAA

ATATCAACTT CAGCTATGAG GTGCTTACCC CTTTGAAGTG GTACCAGAGC    200
TATAGTTGAA GTCGATACTC CACGAATGGG GAAACTTCAC CATGGTCTCG

ATAAGGCCAC CGTACCCTTC CTATGGTTAC GAGCCCATGG GTGGATGGCT    250
TATTCCGGTG GCATGGGAAG GATACCAATG CTCGGGTACC CACCTACCGA

GCACCACCAA ATCATCCCCG TGCTGTCCCA ACAGCACCCC CCGACTCACA    300
CGTGGTGGTT TAGTAGGGGC ACGACAGGGT TGTCGTGGGG GGCTGAGTGT

CCCTGCAGCC TCATCACCAC ATCCAGTGG TGCCAGCTCA GCAGCCCGTG     350
GGGACGTCGG AGTAGTGGTG TAGGGTCACC ACGGTCGAGT CGTCGGGCAC

ATCCCCAGC AACCAATGAT GCCCGTTCCT GGCCAACACT CCATGACTCC     400
TAGGGGGTCG TTGGTTACTA CGGGCAAGGA CCGGTTGTGA GGTACTGAGG

AATCCAACAC CACCAGCCAA ACCTCCCTCC GCCCGCCCAG CAGCCCTACC    450
TTAGGTTGTG GTGGTCGGTT TGGAGGGAGG CGGGCGGGTC GTCGGGATGG

AGCCCCAGCC TGTTCAGCCA CAGCCTCACC AGCCCATGCA GCCCCAGCCA    500
TCGGGGTCGG ACAAGTCGGT GTCGGAGTGG TCGGGTACGT CGGGGTCGGT
```

FIGURE 12

```
GGGTGAGGGC TCATCACCAC ATCCCAGTGG TGCCAGCTCA GCAGCCCGTG  350
GGGAGCTGGG AGTAGTGGTG TAGGGTCACC ACGGTCGAGT CGTCGGGCAC
                                ▲
ATCCCccagc aaccaatgat gcccgttggT GGGGAAGAGT GGATGAGTGG  400
TAGGggtcg ttggttacta cgggcaaGGA GGGGTTGTGA GGTACTCAGG AATCAAAGAG CAGCAGGCAA ACCTGGGTGG GGGGCGGGAG GAGGGTACC  450
TTAGGTTGTG GTCGTCGGTT TGGAGCGAGG GGGGCGGGCT GTGGGATGG AGCCCCAGCC TGTTCAGCCA CAGCCTCACC AGCCCATGCA GCCCAGCCA  500
TCGGGGTCGG ACAGTCGGGT GTCGGAGTGG TCGGGTACGT CGGGTCGGT
                        ◄───

CCTGTGCACC CCATGCAGCC CCTGCCGCCA CAGCCACCTC TGCCTCCGAT  550
```

DETERMINATION OF A GENOTYPE OF AN AMPLIFICATION PRODUCT AT MULTIPLE ALLELIC SITES

RELATIONSHIP TO COPENING APPLICATIONS

This application is a continuation of U.S. Ser. No. 09/018,595, filed Feb. 4, 1998, which is incorporated herein by reference in its entirety.

BACKGROUND OF THE INVENTION

1. Field of the Invention

The invention relates generally to an assay for detecting an amplification product and more specifically to an assay for detecting the genotype of the amplification product at two or more different allelic sites.

2. Description of Related Art

Nucleic acid sequence analysis is becoming increasingly important in many research, medical, and industrial fields, e.g. Caskey, Science 236: 1223–1228 (1987); Landegren et al, Science, 242: 229–237 (1988); and Arnheim et al, Ann. Rev. Biochem., 61: 131–156 (1992). The development of several nucleic acid amplification schemes has played a critical role in this trend, e.g. polymerase chain reaction (PCR), Innis et al, editors, PCR Protocols (Academic Press, New York, 1990); McPherson et al, editors, PCR: A Practical Approach (IRL Press, Oxford, 1991); ligation-based amplification techniques, Barany, PCR Methods and Applications 1: 5–16 (1991); and the like.

PCR in particular has become a research tool of major importance with applications in cloning, analysis of genetic expression, DNA sequencing, genetic mapping, drug discovery, and the like, e.g. Arnheim et al (cited above); Gilliland et al, Proc. Natl. Acad. Sci., 87: 2725–2729 (1990); Bevan et al, PCR Methods and Applications, 1: 222–228 (1992); Green et al, PCR Methods and Applications, 1:77–90 (1991); Blackwell et al, Science, 250: 1104–1110 (1990).

A wide variety of instrumentation has been developed for carrying out nucleic acid amplifications, particularly PCR, e.g. Johnson et al, U.S. Pat. No. 5,038,852 (computer controlled thermal cycler); Wittwer et al, Nucleic Acids Research, 17: 4353–4357 (1989)(capillary tube PCR); Hallsby, U.S. Pat. No. 5,187,084 (air-based temperature control); Garner et al, Biotechniques, 14: 112–115 (1993) (high-throughput PCR in 864-well plates); Wilding et al, International application No. PCT/US93/04039 (PCR in micro-machined structures); Schnipelsky et al, European Patent Application No. 90301061.9 (Publ. No. 0381501 A2)(disposable, single use PCR device), and the like. Important design goals fundamental to PCR instrument development have included fine temperature control, minimization of sample-to-sample variability in multi-sample thermal cycling, automation of pre- and post-PCR processing steps, high speed cycling, minimization of sample volumes, real time measurement of amplification products, minimization of cross-contamination, or sample carryover, and the like.

In particular, the design of instruments that permit PCR to be carried out in closed reaction chambers and monitored in real time is highly desirable. Closed reaction chambers are desirable for preventing cross-contamination, e.g. Higuchi et al, Biotechnology, 10: 413–417 (1992) and 11: 1026–1030 (1993); and Holland et al, PNAS(USA), 88: 7276–7280 (1991). Clearly, the successful realization of such a design goal would be especially desirable in the analysis of diagnostic samples, where a high frequency of false positives and false negatives would severely reduce the value of the PCR-based procedure.

Real time monitoring of a PCR permits far more accurate quantitation of starting target DNA concentrations in multiple-target amplifications, as the relative values of close concentrations can be resolved by taking into account the history of the relative concentration values during the PCR. Real time monitoring also permits the efficiency of the PCR to be evaluated, which can indicate whether PCR inhibitors are present in a sample.

Holland, et al. and others have proposed fluorescence-based approaches to provide measurements of amplification products during a PCR. Holland et al, PNAS(USA), 88: 7276–7280 (1991). Such approaches have either employed intercalating dyes (such as ethidium bromide) to indicate the amount of double stranded DNA present (Higuchi et al, Biotechnology 10:413–417 (1992), Higuchi et al, Biotechnology 11:1026–1030 (1993), U.S. Pat. No. 5,210,015) or they have employed oligonucleotide probes that are cleaved during amplification by 5' nuclease activity of the polymerase to release a fluorescent product whose concentration is a function of the amount of double stranded DNA present, commonly referred to as a 5' nuclease assay. An example of a 5' nuclease assay is the assay used in the Taqman™ LS-50 PCR Detection system (Perkin-Elmer).

In general, 5' nuclease assays employ oligonucleotide probes labeled with at least one fluorescer and at least one quencher. Prior to cleavage of the probe, the at least one fluorescer excites the quencher(s) rather than producing a detectable fluorescence emission. The oligonucleotide probe hybridizes to a target oligonucleotide sequence for amplification in PCR or similar amplification reactions. The 5'→3' nuclease activity of the polymerase used to catalyze the amplification of the target sequence serves to cleave the probe, thereby causing at least one fluorescer to be spatially separated from the one or more quenchers so that the signal from the fluorescer is no longer quenched. A change in fluorescence of the fluorescer and/or a change in fluorescence of the quencher due to the oligonucleotide probe being digested is used to indicate the amplification of the target oligonucleotide sequence.

In 5' nuclease assays, it is often desirable to analyze a sample containing multiple different targets using a different spectrally resolvable species for each target. Such simultaneous detection of multiple targets in a single sample has a number of advantages over serial analysis of each of the targets. Because the sample is analyzed once, fewer steps are required for sample processing and only a single measurement is required. As a result, higher sample throughput and improved user convenience is achieved. In addition, by detecting multiple targets in a single sample, internal calibration is facilitated. An example of a process using simultaneous multispecies spectral detection is multicolor DNA sequencing where four spectrally resolvable fluorescent dyes are simultaneously detected.

One potential application for 5' nuclease assays is in the area of screening for polymorphisms. Current diagnostic techniques for the detection of known nucleotide differences include: hybridization with allele-specific oligonucleotides (ASO) (Ikuta, et al., Nucleic Acids Research 15: 797–811 (1987); Nickerson, et al., PNAS (USA) 87: 8923–8927 (1990); Saiki, et al., PNAS (USA) 86: 6230–6234 (1989); Verlaan-de Vries, et al., Gene 50: 313–320 (1980); Wallace, et al., Nucleic Acids Research 9:879–894 (1981); Zhang, Nucleic Acids Research 19: 3929–3933 (1991)); allele-specific PCR (Gibbs, et al., Nucleic Acids Research 17:

2437–2448 (1989); Newton, et al., Nucleic Acids Research 17: 2503–2516 (1989)); solid-phase minisequencing (Syvanen, et al., American Journal of Human Genetics 1993; 52: 46–59 (1993)); oligonucleotide ligation assay (OLA) (Grossman, et al., Nucleic Acids Research 22: 4527–4534 (1994); Landegren, et al., Science 241: 1077–1080 (1988)); and allele-specific ligase chain reaction (LCR) (Abravaya, et al., Nucleic Acids Research 1995; 23: 675–682; Barany, et al., PNAS (USA) 88:189–193 (1991); Wu, et al., Genomics 4:560–569 (1989)). Genomic DNA is analyzed with these methods by the amplification of a specific DNA segment followed by detection analysis to determine which allele is present.

Lee, et al. has reported using PCR in combination with Taq polymerase to distinguish between different alleles at a single allelic site of the human cystic fibrosis gene. Lee, et al., Nucl. Acids Res. 21:3761–3766 (1993). Livak, et al. has reported distinguishing between alleles in the −23 A/T diallelic polymorphism of the human insulin gene where each allelic site was analyzed in a separate amplification reaction. Livak, et al., Nature Genetics, 9:341–342 (1995). Neither Lee, et al. nor Lival, et al. teach how to distinguish between alleles variants at two or more allelic sites in a single amplification reaction. A need currently exists for a method and instrumentation for distinguishing between multiple sets of substantially homologous sequences, such as allelic variants, in a single amplification reaction. The invention described herein provides such methods and instrumentation.

SUMMARY OF THE INVENTION

The present invention relates to a method for identifying which members of a first set of two or more substantially homologous sequences are present in a sample of DNA and which members of a second, different set of two or more substantially homologous sequences are also present in the sample of DNA. According to the method, the members of the first and second sets present in the sample are identified in a single reaction.

In one embodiment, the method includes the steps of:
performing a nucleic acid amplification on a sample of DNA which includes a first set of substantially homologous sequences and a second, different set of substantially homologous sequences using a nucleic acid polymerase having 5'→3' nuclease activity and one or more primers capable of hybridizing to the sample of DNA in the presence of two or more sets of oligonucleotide probes and amplifying the sets of substantially homologous sequences wherein:
  each set of substantially homologous sequences includes two or more members which each differ from each other at at least one base position,
  each set of oligonucleotide probes is for detecting the members of one of the sets of substantially homologous sequences,
  each set of oligonucleotide probes includes two or more probes which are complementary to different members of a set of substantially homologous sequences, the member being 5' relative to a sequence of the sample DNA to which the primer hybridizes, and
  at least all but one of the oligonucleotide probes include a different fluorescer than the other probes and a quencher positioned on the probe to quench the fluorescence of the fluorescer;
digesting those allelic oligonucleotide probes which hybridize to the target sequence during the amplification by the nuclease activity of the polymerase;
detecting a fluorescence spectrum of the amplification;
calculating a fluorescence contribution of each fluorescer to the fluorescence spectrum; and
determining a presence or absence of the different members of substantially homologous sequences based on the fluorescence contribution of each fluorescer to the fluorescence spectrum.

The present invention also relates to a method for determining a presence or absence of the different allelic variants at the two or more different allelic sites by a 5' nuclease amplification reaction. In one embodiment, the method includes the steps of:
performing a nucleic acid amplification on a sample of DNA having at least two different allelic sites using a nucleic acid polymerase having 5'→3' nuclease activity and at least one primer capable of hybridizing to the sample of DNA and amplifying the at least two different allelic sites in the presence of two or more sets of allelic oligonucleotide probes wherein:
  each set of allelic oligonucleotide probes is for detecting a different allelic site,
  each set of allelic oligonucleotide probes includes two or more probes which are complementary to different allelic variants at the allelic site being detected by the set of probes, the allelic site being 5' relative to a sequence of the sample DNA to which the primer hybridizes, and
  at least all but one of the allelic oligonucleotide probes include a different fluorescer than the other probes and a quencher positioned on the probe to quench the fluorescence of the fluorescer;
digesting those allelic oligonucleotide probes which hybridize to the sample of DNA during the amplification by the nuclease activity of the polymerase;
detecting a fluorescence spectrum of the amplification;
calculating a fluorescence contribution of each fluorescer to the fluorescence spectrum; and
determining a presence or absence of the different allelic variants at the two or more different allelic sites based on the fluorescence contribution of each fluorescer to the fluorescence spectrum.

A method is also provided for genotyping a sample of DNA at at least two allelic sites by a 5' nuclease amplification reaction. In one embodiment, the method includes the steps of:
performing a nucleic acid amplification on a sample of DNA having at least two different allelic sites using a nucleic acid polymerase having 5'→3' nuclease activity and at least one primer capable of hybridizing to the sample of DNA and amplifying the at least two different allelic sites in the presence of two or more sets of allelic oligonucleotide probes wherein:
  each set of allelic oligonucleotide probes is for detecting a different allelic site,
  each set of allelic oligonucleotide probes includes two or more probes which are complementary to different allelic variants at the allelic site being detected by the set of probes, the allelic site being 5' relative to a sequence of the sample DNA to which the primer hybridizes, and
  at least all but one of the allelic oligonucleotide probes include a different fluorescer than the other probes and a quencher positioned on the probe to quench the fluorescence of the fluorescer;
digesting those allelic oligonucleotide probes which hybridize to the target sequence during the amplification by the nuclease activity of the polymerase;

detecting a fluorescence spectrum of the amplification;

calculating a fluorescence contribution of each fluorescer to the fluorescence spectrum; and determining a genotype of the sample of DNA at the at least two different allelic sites based on the fluorescence contribution of the different fluorescers to the fluorescence spectrum.

The present invention also relates to a fluorescence spectrum which is used to genotype a sample of DNA at at least two allelic sites. The spectrum is derived by performing one of the above methods.

The present invention also relates to a fluorescence signature for genotyping a sample of DNA at at least two allelic sites. The signature includes fluorescence signal contributions of at least three fluorescers to a fluorescence spectrum derived by performing one of the above methods.

The present invention also relates to a library of fluorescence signatures for a series of controls, i.e., sequences having known allelic variants at at least two allelic sites. The library of fluorescence signatures can be used to determine which allelic variants are present in a sample of DNA whose genotype is being determined.

The present invention also relates to a method for determining a fluorescence signature of a sample of DNA. According to one embodiment, fluorescence contributions of at least three fluorescers to a fluorescence spectrum taken from a nucleic acid amplification are calculated and normalized relative to an internal standard, the normalized fluorescence contributions corresponding to a fluorescence signature for the sample of DNA for the at least two different allelic sites.

The present invention also relates to a method for genotyping a sample of DNA by comparting the fluorescence signature of the DNA sample to control sequences having known genotypes.

The present invention also relates to a processor and related instrument for genotyping a sample of DNA at at least two allelic sites by a 5' nuclease assay. In one embodiment, the processor includes logic for taking fluorescence spectra of control samples and at least one unknown sample which have undergone a 5' nuclease assay in the presence of allelic probes for the at least two allelic sites and fluorescence spectra of at least three fluorescers used in the 5' nuclease assay and using these spectra to calculate normalized fluorescence contributions of the at least three fluorescers to the unknown and control fluorescence spectra; and logic for determining a genotype of the at least one unknown sample at two or more different allelic sites based on a comparison of the normalized fluorescence contributions of the at least three fluorescers to the spectrum of the unknown sample and normalized fluorescence contributions to the spectra of the control samples.

The present invention also relates to a kit for determining which members of at least two different sets of substantially homologous sequences are present in a sample of DNA. According to one embodiment, the kit includes two or more sets of oligonucleotide probes wherein:

each set of oligonucleotide probes is for detecting a different set of substantially homologous sequences, each set of oligonucleotide probes includes two or more probes which are complementary to different members of a set of substantially homologous sequences, and at least all but one of the allelic oligonucleotide probes include a different fluorescer than the other probes and a quencher positioned on the probe to quench the fluorescence of the fluorescer.

The present invention also relates to a kit for genotyping a sample of DNA at at least two allelic sites. In one embodiment, the kit includes two or more sets of allelic oligonucleotide probes wherein:

each set of allelic oligonucleotide probes is for detecting a different allelic site, each set of allelic oligonucleotide probes includes two or more probes which are complementary to different allelic variants at the allelic site being detected by the set of probes, and at least all but one of the allelic oligonucleotide probes include a different fluorescer than the other probes and a quencher positioned on the probe to quench the fluorescence of the fluorescer.

Optionally, the allelic probes are complementary to allelic sites on a target sequence which are separated by between about 50 and 150 bases, more preferably less than 100 bases. The allelic probes optionally have a % GC of at least about 20% and less than about 80%. All of the allelic probes optionally have less than four contiguous guanines. In one embodiment, none of the allelic probes have a guanine at the 5' end.

In one variation of the above kit embodiments, the probes have a melting point temperature ($T_m$) that is about 3–5° C. greater than the annealing temperature used in the amplification reaction. In another variation, the probes have melting point temperatures about 65–70° C., more preferably about 65–67° C.

In one variation of the above kit embodiments, the kit also includes one or more amplification primers. In one variation, the probe melting point temperature ($T_m$) is about 5–10° C. greater than the primer's $T_m$, and preferably about 7° C. greater. In another variation, the primers have a melting point temperature ($T_m$) of about 55–65° C., preferably about 58–63° C., more preferably about 58–60° C. The primer preferably has two or less guanines or cytosines among the five nucleotides at a 3' end of the primer.

BRIEF DESCRIPTION OF THE FIGURES

FIG. 1A illustrates the polymerization of forward and reverse primers.

FIG. 1B illustrates strand displacement of the fluorescer-quencher probe by the 5'→3' nuclease activity of a nucleic acid polymerase.

FIG. 1C illustrates cleavage of the fluorescer by the polymerase.

FIG. 1D illustrates completion of the amplification of the target sequence.

FIGS. 4A–4D illustrates how fluorescer-quencher probes for two or more different allelic sites and a 5' nuclease assay can be used to genotype a target sequence at the two or more different allelic sites.

FIG. 4A illustrates a nucleic acid amplification reaction being performed on a target sequence having two allelic sites using a nucleic acid polymerase having 5'→3' nuclease activity and a primer capable of hybridizing to the target sequence.

FIG. 4B illustrates the nucleic acid polymerase extending the forward and reverse primers.

FIG. 4C illustrates extension of the primers continuing and the polymerase performing strand displacement.

FIG. 4D illustrates the fluorescers and quenchers attached to the digested allelic probes being displaced from the target sequence.

FIGS. 5A–5C illustrates how fluorescer-quencher probes for two or more different allelic sites and a 5' nuclease assay can be used to genotype a sample of DNA at two or more different allelic sites using a different primer for each allelic site.

FIG. 5A illustrates a nucleic acid amplification reaction being performed on a DNA sequence using a nucleic acid polymerase having 5'→3' nuclease activity and two primers capable of hybridizing to different DNA sequences.

FIG. 5B illustrates the nucleic acid polymerase extending the primers and releasing fluorescers for the different allelic sites.

FIG. 5C illustrates the fluorescers and quenchers attached to the digested allelic probes being displaced from the DNA.

FIGS. 6A and 6B illustrate the impact of having longer or shorter distances between the primer and probe.

FIG. 6A illustrates the sequence of a double stranded amplicon with inner and outer primers for amplification of the double stranded amplicon.

FIG. 6B illustrates amplification curves comparing the fluorescence signal generated when different combinations of primers and probes are used.

FIGS. 8A and 8B illustrate sequences for Amelogenin X and Amelogenin Y respectively from which an amplicon, primers and probe are to be determined.

FIG. 9 illustrates a comparison of a portion of Amelogenin X to a portion of Amelogenin Y where the symbol | between the sequences indicates that the two sequences have the same nucleotide at the particular base position and the symbol - between the sequences indicates that the two sequences have a different nucleotide at the particlar base position.

FIG. 10 illustrates a portion of Amelogenin X (bases 50–750) with the allelic site to be identified by the 5' nuclease assay illustrated in bold.

FIG. 11 illustrates bases 251–500 of Amelogenin X illustrated in FIG. 10 along with its complementary (antisense) strand.

FIG. 12 illustrates the Amelogenin X amplicon selected by this process.

DEFINITIONS

Figure 1:
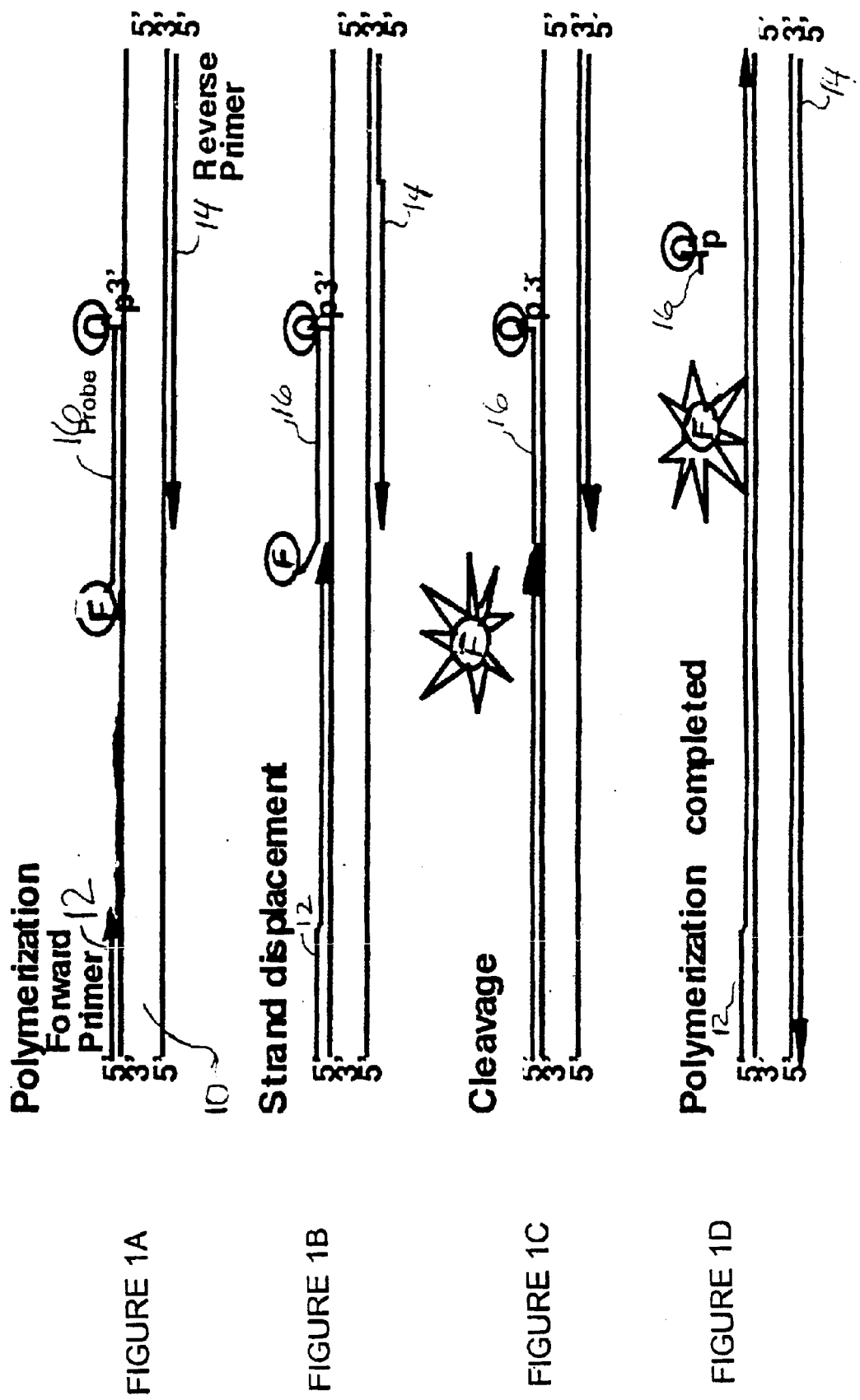
FIGS. 1A–1D illustrate the steps of a 5' nuclease assay.

As used in this application, the term "oligonucleotide" includes linear oligomers of natural or modified monomers or linkages, including deoxyribonucleosides, ribonucleosides, and the like; capable of specifically binding to other oligonucleotide sequences by way of a regular pattern of monomer-to-monomer interactions, such as Watson-Crick type of basepairing, or the like. Usually monomers are linked by phosphodiester bonds or analogs thereof to form oligonucleotides ranging in size from a few monomeric units, e.g., 3–4, to several tens of monomeric units. Whenever an oligonucleotide is represented by a sequence of letters, such as "ATGCCTG", it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like.

"Target oligonucleotide sequence" refers to the sequence which is amplified according to the present invention in order to determine its genotype. The target oligonucleotide sequence is also referred to as the amplicon of the 5' nuclease assay.

"Oligonucleotide probe" refers to the oligonucleotide sequence containing at least one fluorescer and at least one quencher which is digested by the 5' endonuclease activity of the polymerase in order to detect any amplified target oligonucleotide sequences. In general, the oligonucleotide probes used in the invention will have a sufficient number of phosphodiester linkages adjacent to its 5' end so that the 5'→3' nuclease activity employed can efficiently degrade the bound probe to separate the fluorescers and quenchers.

"Perfectly matched" in reference to a duplex means that the oligonucleotide strands making up the duplex form a double-stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. Conversely, a "mismatch" in a duplex between a target oligonucleotide sequence and an oligonucleotide probe or primer means that a pair of nucleotides in the duplex fails to undergo Watson-Crick bonding.

"Substantially homologous sequences" refers to two or more sequences (or subregions of a sequence) which are homologous except for differences at one or more base positions. Two allelic variants which differ by only one nucleotide is an example of a set of substantially homologous sequences. The substantially homologous sequences are preferably at least 90% homologous.

As used in the application, "nucleoside" includes the natural nucleosides, including 2'-deoxy and 2'-hydroxyl forms, e.g., as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g., described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce degeneracy, increase specificity, and the like.

DETAILED DESCRIPTION

The present invention relates to a 5' nuclease assay in which a first set of fluorescer-quencher probes is used to identify which members of a first set of two or more substantially homologous sequences are present in a sample of DNA and a second set of fluorescer-quencher probes is used in the same reaction to identify which members of a second set of two or more substantially homologous sequences are also present in the sample of DNA. The 5' nuclease assay is performed in a single reaction containing both the first and second sets of probes. The assay enables one to determine which members of first set of substantially homologous sequences are present in the sample while simultaneously enabling one to determine which members of second set of substantially homologous sequences are present in the sample.

One application of the 5' nuclease assay is determining the genotype of a sample of genomic DNA at the two or more different allelic sites. The two or more different allelic sites may be on a single strand of DNA or may be on different strands of DNA. The two or more different allelic sites may be amplified by a single amplification primer, for example when the allelic sites are on the same strand of DNA and adjacent each other, or by multiple different amplification primers.

The present invention also relates to a 5' nuclease assay adapted to determine the allelic genotype of a sample of DNA at multiple allelic sites, devices and kits for performing the assay, and the fluorescence spectrum and fluorescence signature produced by performing the assay. The present invention also relates to devices, logic and software used to analyze the fluorescence spectrum and fluorescence signature produced by performing the assay.

As will be explained herein in greater detail, performance of the assay of the present invention produces a fluorescence spectrum which is characteristic of a sample of DNA which includes a particular combination of members of the multiple sets of the two or more substantially homologous sequences in the sample of DNA. For example, when used to determine the genotype of a sample of DNA at two or more allelic sites, performance of the assay produces a fluorescence spectrum which is characteristic of a sample of DNA having that genotype which has been subjected to the assay, i.e., using the particular temperatures, primers and probes used to perform the assay. By calculating a contribution of the different fluorophores (fluorescers and quenchers) used in assay to the fluorescence spectrum, a fluorescence signature can be produced which is characteristic of a sample of DNA. The fluorescence signature of a given unknown sample can then be compared to that of samples having the various different known combinations of members in order to determine which members of the two or more sets are present in the sample. For example, when genotyping an unknown sample, the fluorescence signature produced as a result of performing the assay can be compared to the fluorescence signatures of the various known genotypes in order to determine the genotype of the unknown sample.

1. 5' Nuclease Assay for Measuring Amplification Products

The present invention utilizes a variation of a 5' nuclease assay in order to determine the presence of members of two different sets of substantially homologous sequences in a sample of DNA. In general, a 5' nuclease assay involves the digestion of an oligonucleotide probe containing a fluorescer and quencher during a nucleic acid amplification reaction to evidence the amplification of a particular member.

FIGS. 1A–1D illustrate the steps of a 5' nuclease assay. In the assay, a nucleic acid amplification reaction is performed on a target sequence (double stranded sequence 10) using a nucleic acid polymerase (not shown) having 5'→3' nuclease activity and a primer (forward and reverse primers 12, 14) capable of hybridizing to the target sequence 10 in the presence of an oligonucleotide probe 16 which is capable of hybridizing to the target sequence downstream relative to one of the primers. As illustrated in FIG. 1A, the oligonucleotide probe 16 includes a fluorescer (F) and quencher (Q). The binding site of the oligonucleotide probe 16 is located upstream (5') relative to the binding site for the forward primer 12 used to amplify the target sequence 10. The oligonucleotide probe 16 is preferably constructed such that the polymerase can not extend the 3' end of the probe. This may be accomplished by attaching the fluorescer or quencher to the terminal 3' carbon of the oligonucleotide probe by a linking moiety.

As illustrated in FIG. 1B, the nucleic acid polymerase (not shown) extends the forward and reverse primers 12, 14. Preferably, PCR is carried out using a Taq DNA polymerase, e.g., AMPLITAQ™ or AMPLITAQ™ Gold (Perkin-Elmer, Norwalk, Conn.), or an equivalent thermostable DNA polymerase.

During extension of the primer, the polymerase encounters the probe hybridized to the target sequence and performs strand displacement by digesting the probe. As illustrated in FIG. 1C, digestion of the probe results in release of the fluorescer (or quencher) from the probe. This causes the fluorescer and quencher on the probe to become spatially separated from each other, thereby creating a change in fluorescence in the sample to indicate the extension of the primer 12 and hence the amplification of the target sequence 10. As illustrated in FIG. 1D, both the fluorescer and quencher are ultimately displaced from the target sequence.

Detailed descriptions of nucleic acid amplification reactions employing fluorescer-quencher probes can be found in many publications, including, for example, Holland, et al., PNAS (USA) 88:7276–7280 (1992); Holland, et al., Clinical Chemistry, 38:462–463 (1992); Lee, et al., Nucleic Acid Research, 21: 3761–3766 (1993), Livak, et al., PCR Methods and Applications, 4:357–362 (1995) and U.S. application Ser. No. 08/559,405 which is incorporated herein by reference.

As used herein, the fluorescer can be any molecule capable of generating a fluorescence signal. The quencher molecule can be any molecule capable of absorbing the fluorescence energy of the excited fluorescer, thereby quenching the fluorescence signal that would otherwise be released from the excited fluorescer. In order for a quencher molecule to quench an excited fluorescer, the quencher must generally be within a minimum quenching distance of the excited fluorescer at some time prior to the fluorescer releasing the stored fluorescence energy.

A variety of different fluorescer-quencher probes have been developed for use in this method. Initially, probes were developed where the fluorescer and quencher were always in close proximity with each other on the probe so that the quencher efficiently quenched the fluorescer. The design of fluorogenic probes has since been simplified by the discovery that probes with a reporter dye on the 5' end and a quencher dye on the 3' end exhibit adequate quenching for performance in the 5' nuclease assay. Livak, et al., PCR Methods and Applications 4: 357–362 (1995). For example, probes have been developed where the fluorescer and quencher are positioned such that they exist in at least one single-stranded conformation when unhybridized where the quencher molecule quenches the fluorescence of the fluorescer and exist in at least one conformation when hybridized to a target oligonucleotide sequence where the fluorescence of the fluorescer is unquenched. See application Ser. No. 08/559,405 (incorporated herein by reference). As a result, the fluorescer and quencher need not be positioned at a specific distance within a probe in order to achieve effective quenching to be detected. This facilitates the design and synthesis of these probes.

Probes have also been developed where the probe hybridizes to itself to form a loop such that the quencher molecule is brought into proximity with the fluoescer in the absence of a complementary nucleic acid sequence to prevent the formation of the hairpin structure. WO 90/03446; European Patent Application No. 0 601 889 A2.

Any of the above fluorescer-quencher probes can be used in conjunction with the present invention.

It might be expected that probes described in Livak, et al., WO 90/03446, or European Patent Application No. 0 601 889 A2 where the distance between the fluorescer and quencher is increased would compromise the ability of a probe to discriminate against mismatches. However, it has been demonstrated that even probes with a reporter at the 5' end and a quencher at the 3' end can be used to distinguish alleles. Livak, et al., Nature Genetics, 9:341–342 (1995).

Figure 2:
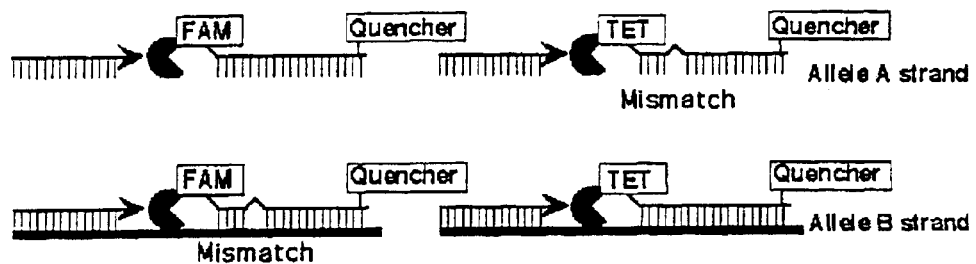
FIG. 2 illustrates how the 5' nuclease assay can be used to identify the genotype of a target sequence at a single allelic site.

FIG. 2 illustrates how a 5' nuclease assay can be used to identify the genotype of a target sequence at a single allelic site. As illustrated in the figure, probes specific for allele A and allele B are included in the PCR assay. The probes can be distinguished by labeling each with a different fluorescent reporter dye, illustrated in the figure as FAM (6-carboxyfluorescein) and TET (6-carboxy4,7,2',7'-tetrachlorofluorescein). A mismatch between the probe and target sequence greatly reduces the efficiency of probe hybridization and cleavage.

Figure 3:
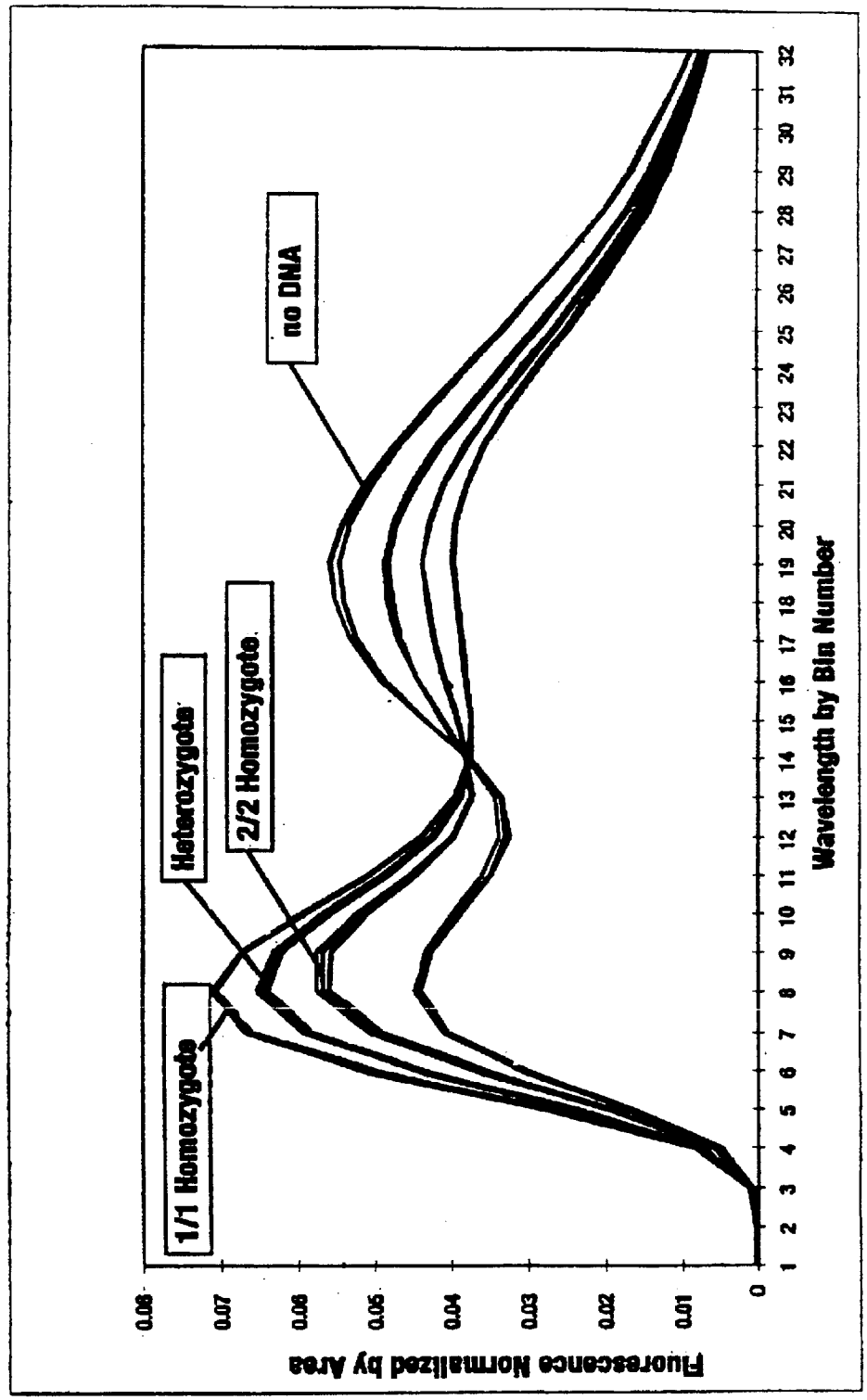
FIG. 3 shows fluorescence spectra observed in an allelic discrimination experiment such as the one illustrated in FIG. 2.

FIG. 3 shows fluorescence spectra observed in an allelic discrimination experiment such as the one illustrated in FIG. 2. In this figure, each of the three possible genotypes (homozygote for allele A; homozygote for allele B; heterozygote for alleles A and B) has a spectrum distinct from each other and from the spectrum of unreacted probe (no DNA). By comparing these spectra to that of an unknown sample, the genotype of the unknown sample can be determined. For example, a substantial increase in the FAM or TET fluorescent signal indicates homozygosity for the allele that is complementary to the probe containing the fluorescer whose signal increased. An increase in both FAM and TET signals indicates heterozygosity.

The fluorescence spectra of FAM and TET have significant overlap. As can be seen from FIG. 3, it is difficult to distinguish between a spectrum having a strong FAM signal (1/1 homozygote), a spectrum having a strong TET signal (2/2 homozygote), and a spectrum having a moderate FAM and TET signals (heterozygote). The use of additional allelic probes having additional fluorescers in the same assay would further complicate the differentiation of fluorescence spectra derived from different genotypic samples. As will be described herein, Applicants provide an assay for determining the genotype of a target sequence at multiple allelic sites using at least four allelic probes having a total of at least three different fluorescers by determining a fluorescence signature for each sample based on the fluorescence spectra produced via the 5' nuclease assay.

2. 5' Nuclease Assay for Genotyping Amplification Products at Multiple Allelic Sites The present invention relates to an adaption of a 5' nuclease assay, such as the assay illustrated in FIGS. 1A–1D, to determine the presence of members of two different sets of substantially homologous sequences in a sample of DNA in a single assay. While the present invention will now be described with regard to the detection of a multiple allelic genotype of a sample of genomic DNA, it is noted that the invention is not intended to be limited to this particular application but rather is intended to be applicable generically to the identification of members of multiple sets of two or more substantially homologous sequences in a sample of DNA.

FIGS. 4A–4D and 5A–5D illustrate how fluorescerquencher probes for two or more different allelic sites and the 5' nuclease assay can be used to genotype a sample of DNA at the two or more different allelic sites. It is noted that DNA for only a single genotype is illustrated in FIGS. 4A–4D and 5A–5D. It should be noted that if a sample of DNA contains DNA for more than one genotype, i.e., a heterozygote, different groups of probes will hybridize to the DNA for each genotype.

FIGS. 4A–4D illustrate performance of the 5' nuclease assay where the two or more different allelic sites are sufficiently near each other on the same strand of DNA such that it is possible to amplify both allelic sites with a single primer. FIGS. 5A–5D illustrate the performance of the 5' nuclease assay where the two or more different allelic sites are amplified using different primers.

As illustrated in FIG. 4A, a nucleic acid amplification reaction is performed on a target sequence (double stranded sequence 40) using a nucleic acid polymerase (not shown) having 5'→3' nuclease activity and a primer (forward and reverse primers 42, 44) capable of hybridizing to the target sequence 40. The amplification reaction is performed in the presence of a first set of allelic probes 46A, 46B for a first allelic site 47 and a second set of allelic probes 48A, 48B for a second allelic site 49. Each set of allelic probes includes at least two probes which differ from each other by at least one nucleotide.

All of the allelic probes are complementary to allelic sites on the target sequence which are upstream (5') relative to the sequence to which one of the primers is complementary. As illustrated in FIG. 4A, all but one of the allelic probes includes a different fluorescer ($F_1$, $F_2$, $F_3$) and a quencher (Q). The allelic probe 48B which does not include a fluorescer optionally can include a fluorescer. The fluorescer on allelic probe 48B should be different than the other fluorescers (i.e., $F_4$).

As illustrated in FIG. 4A, one of the probes from the first set (46A) hybridizes to the first allelic site 47 and one of the probes from the second set (48A) hybridizes to the second allelic site 49. While only one probe from each set is shown to hybridize to a particular allelic site, it should be noted that other probes of the set can also hybridize to the site. In this regard, the different allelic probes of each set compete to hybridize to the allelic site. The allelic probe which perfectly matches the allelic site will be thermodynamically favored for hybridizing to the allelic site over probes in the set which include a mismatch. In addition, it has been found that cleavage of the allelic probe by the polymerase is more efficient for perfectly matched allelic probes than for allelic probes with a mismatch.

As illustrated in FIG. 4B, the nucleic acid polymerase (not shown) extends the forward and reverse primers 42, 44. Preferably, PCR is carried out using a Taq DNA polymerase, e.g., AMPLITAQ™ or AMPLITAQ™ Gold (Perkin-Elmer, Norwalk, Conn.), or an equivalent thermostable DNA polymerase.

During extension of the primers 42, 44, the polymerase encounters whichever allelic probe is hybridized to the first allelic site (illustrated as probe 46A) and performs strand displacement by beginning to digest that probe. As illustrated in FIG. 4B, digestion of that probe results in the release of the fluorescer (shown as $F_1$) attached to that digested allelic probe.

As illustrated in FIG. 4C, extension of the primers continues and the polymerase encounters whichever allelic probe is hybridized to the second allelic site (illustrated as probe 48A) and performs strand displacement by digesting that probe. As illustrated in FIG. 4C, digestion of that probe results in the release of the fluorescer (shown as $F_3$) attached to that digested allelic probe.

As illustrated in FIG. 4D, both the fluorescers and quenchers attached to the digested allelic probes are ultimately displaced from the target sequence.

A fluorescence spectrum of the sample is taken after at least one amplification cycle which reflects the relative number of the different fluorescers and quenchers which have been released.

Figure 5C:
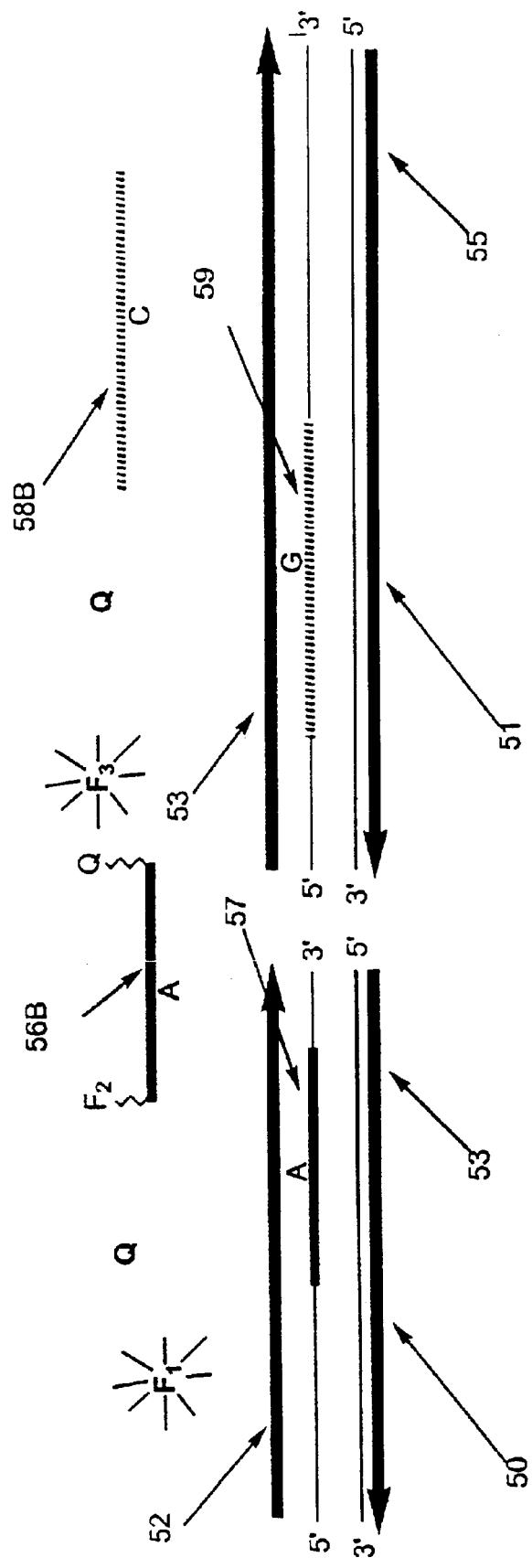

FIGS. 5A–5C illustrate the performance of the 5' nuclease assay where the two or more different allelic sites are amplified using different primers. As illustrated in FIG. 5A, a nucleic acid amplification reaction is performed on a two separate sequences (double stranded sequences 50, 51) using a nucleic acid polymerase (not shown) having 5'→3' nuclease activity and primers (forward 52, 53 and reverse primers 54, 55) capable of hybridizing to each target sequence 50, 51. It is noted that if the two or more different allelic sites were positioned on the same strand, the amplification could also be performed using a single pair of primers, as illustrated in FIGS. 4A–4D, or using multiple primers.

The amplification reaction is performed in the presence of a first set of allelic probes 56A, 56B for a first allelic site 57 and a second set of allelic probes 58A, 58B for a second allelic site 59. Each set of allelic probes includes at least two probes which differ from each other by at least one nucleotide.

All of the allelic probes are complementary to allelic sites on the target sequence which are upstream (5')relative to the sequence to which one of the primers is complementary. As illustrated in FIG. 5A, all but one of the allelic probes includes a different fluorescer ($F_1$, $F_2$, $F_3$) and a quencher (Q). The allelic probe 58B which does not include a fluorescer optionally can include a fluorescer. The fluorescer on allelic probe 58B should be different than the other fluorescers (i.e., $F_4$).

As illustrated in FIG. 5A, one of the probes from the first set (56A) hybridizes to the first allelic site 57 and one of the probes from the second set (58A) hybridizes to the second allelic site 59. While only one probe from each set is shown to hybridize to a particular allelic site, it should be noted that other probes of the set can also hybridize to the site.

As illustrated in FIG. 5B, the nucleic acid polymerase (not shown) extends the forward and reverse primers 52, 53, 54, and 55. Preferably, PCR is carried out using a Taq DNA polymerase, e.g., AMPLITAQ™ or AMPLITAQ™ Gold (Perkin-Elmer, Norwalk, Conn.), or an equivalent thermostable DNA polymerase.

During extension of the primers, the polymerase encounters whichever allelic probe is hybridized to the first allelic site (illustrated as probe 56A) and performs strand displacement by beginning to digest that probe. The polymerase also encounters whichever allelic probe is hybridized to the second allelic site (illustrated as probe 58A) and performs strand displacement by beginning to digest that probe. As illustrated in FIG. 5B, digestion of that probe results in the release of fluorescers (shown as $F_1$, $F_3$) attached to the digested allelic probes.

As illustrated in FIG. 5C, both the fluorescers and quenchers attached to the digested allelic probes are ultimately displaced from the sequence being amplified.

A fluorescence spectrum of the sample is taken after at least one amplification cycle which reflects the relative number of the different fluorescers and quenchers which have been released.

A number of factors contribute to the assay's ability to discriminate between perfectly matched allelic probes and probes with only a single mismatch, even a single mismatch within a probe that is 20–30 nucleotides long. A mismatch has a disruptive effect on hybridization which make perfectly matching probes thermodynamically favored over mismatched probes. For example, a mismatched probe will have a lower melting temperature ($T_m$) than a perfectly matched probe. Multiple mismatches have an even greater disruptive effect on hybridization than single mismatches. As a result, multiple mismatch probes are even less thermodynamically favored than perfectly matched probes.

Proper choice of an annealing/extension temperature in the PCR will favor hybridization of an exact-match probe over a mismatched probe. The thermal window defining this choice is bracketed by the thermal transitions for the binding of a probe to its homologous or heterologous targets. By raising or lowering the annealing temperature, discrimination against a mismatch can be increased or reduced respectively.

One of the features of the 5' nuclease assay which enables its use for distinguishing between different substantially homologous sequences at multiple different sites (such as identifying different alleles at multiple allelic sites) is the inefficient cleavage of probes when there is even a single mismatch within a probe that is 20–30 nucleotides long.

It is also important to note that the assay is performed under competitive conditions. Multiple probes to the same allelic site are present in the same reaction vessel. Part of the discrimination against a mismatch is that the probe that is perfectly matched functions to prevent the mismatched probe from binding because of the perfectly matched probe's stable hybridization to the sequence being amplified.

The 5' end of the allelic probe must also be displaced before it is cleaved. The 5' nuclease activity of Taq DNA polymerase is believed to recognize a forked structure with a displaced 5' strand of 1–3 nucleotides. Landegren, et al., Science 241: 1077–1080 (1988). Once probe displacement starts, complete dissociation will be significantly faster with a less thermodynamically stable mismatched probe than it will be with a perfectly matched probe. As a result, cleavage of a mismatched probe by a polymerase is significantly less efficient than is cleave of a perfectly matched allelic probe.

A key advantage of the present invention for determining the genotype of a sample of DNA at multiple allelic sites is that it does not rely on the 5' nuclease assay working with 100% efficiency to distinguish between substantially homologous sequences such as alleles, i.e., where only perfectly matched allelic probes are cleaved and no mismatched allelic probes are cleaved. Rather, the present invention assumes that a certain degree of inefficiency occurs and relies on that degree of inefficiency to be highly consistent sample to sample. By generating a fluorescence spectrum and a fluorescence signature for each genotype which uniquely reflects the assay's inherent inefficiency for that genotype given the particular conditions, probes and primers used, the genotype of unknown sequences can be determined.

3. Generating an Allelic Fluorescence Signature from a 5' Nuclease Assay

An important aspect of the present invention is the processing of a fluorescence spectrum generated by performing the 5' nuclease assay in order to determine which members of the sets of substantially homologous sequences are present, for example, in order to determine the genotype of a genomic sample of DNA. As illustrated in FIGS. 4A–4D and 5A–5D, the fluorescence signal generated by the fluorescers and quenchers present in the reaction mixture will change as the DNA sample is amplified and several of the allelic probes are digested. The fluorescence signal from the reaction mixture will include contributions from the different fluorescers ($F_1$, $F_2$ and $F_3$), the quencher, as well as from an internal standard. In order to determine which allelic probes were digested and what genotype is present, it is necessary to unravel the different contributions of the allelic probes and their fluorescent components to that spectrum.

The first step in the analysis of a fluorescence signal derived from a 5' nuclease reaction is the creation of a reference library of spectra of the fluorescers and quenchers on the allelic probes used in the 5' nuclease assay. These spectra are expressed as normalized 1×n matrixes of fluorescence intensity values where n represents fluorescence measurements at a series of n wavelengths, n preferably being 32 values. The matrixes are normalized by setting the largest value in the matrix to 1. The reference library of spectra and their associated 1×n matrixes can be stored in a database or taken at the time of analysis.

A 5' nuclease assay is then performed on a series of samples including samples containing genomic DNA whose genotype is known ("Control"); samples containing genomic DNA whose genotype is unknown ("Unknowns"); and samples containing no template ("NT"). Fluorescence spectra are taken of the control and unknown samples and expressed as 1×n matrixes of fluorescence intensity values where n represents fluorescence measurements at a series of n wavelengths, n preferably being 32 values. The matrixes may optionally be normalized by setting the largest value in the matrix to 1.

The 1×n matrixes representing the fluorescent spectra of the control and unknown spectra are then analyzed to determine the relative fluorescent contributions of the fluorescent species present in the 5' nuclease assay using the 1×n matrix representations of the reference library spectra. Determination of the relative fluorescent contributions of the different fluorescent species can be performed by the multicomponent analysis method described in application Ser. No. 08/659,115 entitled "MULTICOMPONENT ANALYSIS METHOD INCLUDING THE DETERMINATION OF A STATISTICAL CONFIDENCE INTERVAL" which is incorporated herein by reference.

Once the relative fluorescent contributions of the different fluorescent species are determined, the contributions of the different fluorescent species are normalized using a passive fluorescent internal standard. The internal standard is passive in the sense that its fluorescence does not significantly change during a nucleic acid amplification reaction. The use of an internal standard in nucleic acid amplification reactions and for normalizing fluorescence spectra is described in application Ser. No. 08/657,989 entitled "PASSIVE INTERNAL REFERENCES FOR THE DETECTION OF NUCLEIC ACID AMPLIFICATION PRODUCTS" which is incorporated herein by reference.

The normalized contributions of the different fluorescent species to the control and unknown's fluorescence spectra correspond to their "fluorescence signatures." The term "fluorescence signature" is used herein to describe the relative contributions of the different fluorescent species to the spectra produced by performance of the 5' nuclease assay because the relative contributions can be used to distinguish the spectra of the different controls from each other and can also be used to identify the genotype of an unknown sample of DNA based on a comparison of the relative contributions to the spectrum for the unknown to the relative contributions to the spectra for the different controls. It is noted that the fluorescence signature is not only dependent on which members of the sets of substantially homologous sequences present in the sample (e.g., which allelic variants are present) but is also dependent on a series of assay dependent variables including the given 5' nuclease assay conditions (time, temperature), the probes, primers and polymerase used, the relative hybridization competition between the probes and the algorithm used to calculate the contribution of the different fluorescent species. As an example of the present invention, the determination of fluorescence signatures for ApoE genotyping is described below.

4. Determining Genotype at Multiple Allelic Sites from Fluorescence Signature Once fluorescence signatures of the controls, unknowns, and NT are determined, the fluorescence signature of each unknown is compared to the fluorescence signatures of each of the controls and the NT in order to genotype each unknown. If the amplification reaction was successful, the fluorescence signature of the unknown should match the fluorescence signature of a single control or a 50—50 mixture of two controls for a heterozygote. If the amplification reaction was unsuccessful, the fluorescence signature of the unknown will not match any of the controls and should match the NT signature. As an example of the present invention, the determination of ApoE genotypes from fluorescence signatures is described below.

5. Kit for Performing Fluorescer-quencher Probe Assay to Determining Genotype of Amplified Product at Multiple Allelic Sites The present invention also relates to a kit for determining which members of at least two different sets of substantially homologous sequences are present in a sample of DNA. As an example, the kit may be for determining the genotype of a sample of genomic DNA at at least two different allelic sites using a 5' nuclease assay. The kit may also be for differentiating between two or more sets of two or more substantially homologous sequences where the substantially homologous sequences are not related to each other as allelic variants, for example, sequences from different strains of microorganisms.

According to one embodiment, the kit includes at least two sets of probes where each set of probes is for distinguishing between two or more substantially homologous sequences, the two or more substantially homologous sequences differing from each other by at least one nucleotide, and each probe in the set perfectly matching one of two or more substantially homologous sequences. The kit may optionally also include additional sets of probes, amplification primers and/or a polymerase for use in the assay. Combined, the probes of the two or more sets include at least three different fluorescers. One probe may optionally not include a fluorescer or include a fluorescer which is present in a different set. The at least two sets of probes should be selected so as to produce distinguishable fluorescence signatures for the different genotypes being detected.

In another embodiment, the kit includes at least a first set of allelic probes for genotyping a first allelic site and second set of allelic probes for genotyping a second allelic site. The kit may optionally also include additional sets of allelic probes, amplification primers and or a polymerase for use in the assay. Each set of probes includes at least two probes which are capable of hybridizing to the allelic site but differ from each other by at least one nucleotide. Combined, the allelic probes of the two or more sets include at least three different fluorescers. One probe may optionally not include a fluorescer or include a fluorescer which is present in a different set. The at least two sets of probes should be selected so as to produce distinguishable fluorescence signatures for the different genotypes being detected.

The kit may also include sample DNA which can serve as a control in the assay. For example, the sample DNA can include specific members of the substantially homologous sequences. In one embodiment, the sample DNA has a known genotype at first and second allelic sites. The kit may also include a fluorescent material for use as a passive internal standard. Optionally, the kit may also include buffer or other reagents for performing the 5' nuclease assay.

6. Guidelines for Performing a 5' Nuclease Assay

The following guidelines have been developed for performing a 5' nuclease assay such as the assay used in the present invention to detect the genotype of a sample of DNA at an allelic site. Using a native sequence which includes one of the homologous sequences to be identified, the guidelines assist one of ordinary skill in the selection of the primer sequences, probe sequences and the section of sequence to be amplified (the amplicon) in the assay.

A. Primer and Probe Design Guidelines

I. Amplicon Length and Primer-Probe Separation

The operation of the 5' nuclease assay has been found to improve as the length of the sequence being amplified decreases. Consistent and predictable results have been routinely obtained for amplicons as short as 50 bp and as long as 150 bp. Longer amplicons may also yield acceptable results but will not necessarily provide the predictable and reproducible performance which the optimization strategy described herein provides. Forward and reverse primers should be designed to be positioned as close as possible to each allelic oligonucleotide probe. As the distance between the primers and allelic probes or the overall amplicon length increase, performance of the assay decreases and the reaction becomes more difficult to optimize.

Figure 6B:
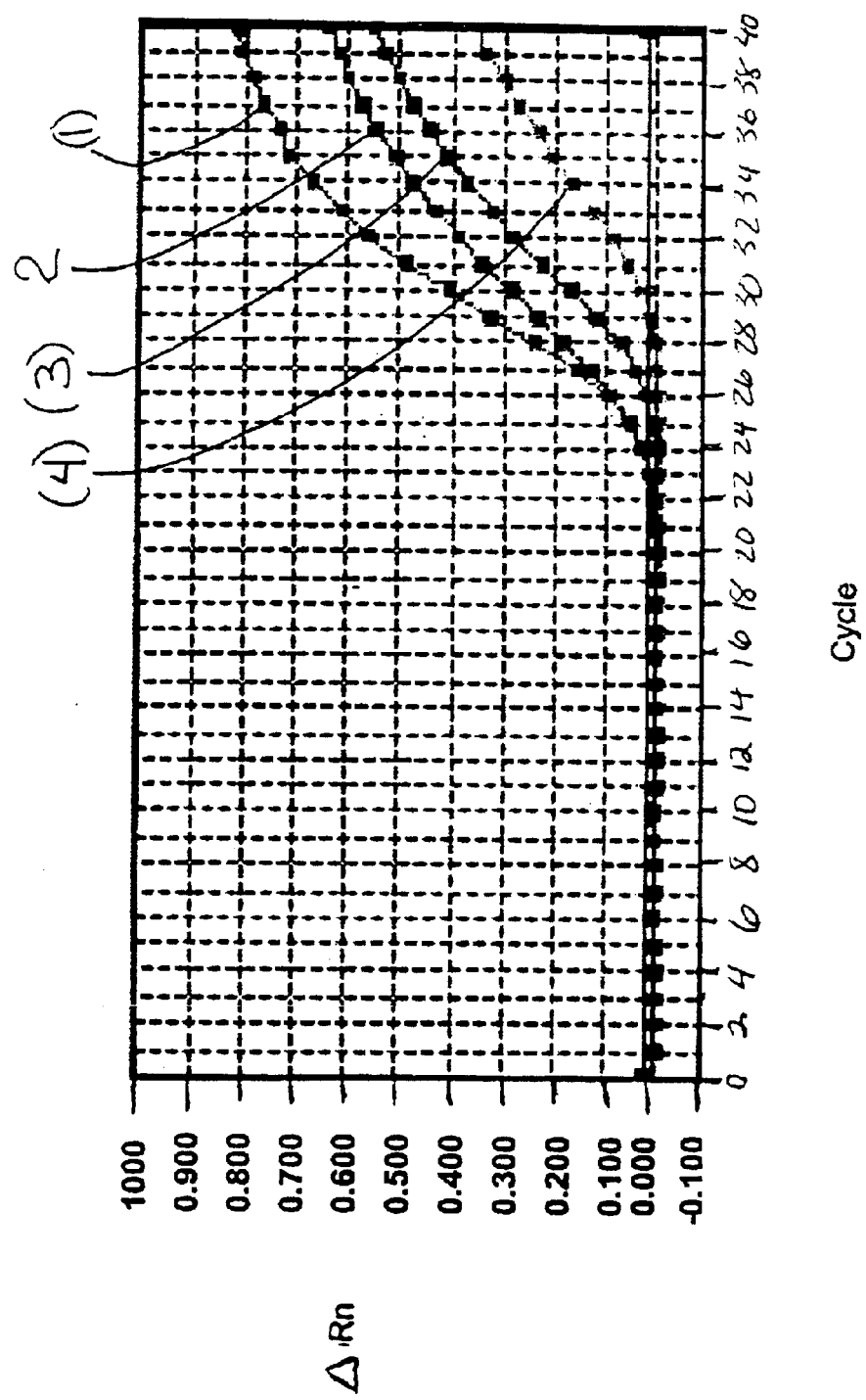

The impact of having longer or shorter distances between the primer and probe is illustrated in FIGS. 6A and 6B. FIG. 6A illustrates the sequence of a double stranded amplicon 62. Also illustrated are sequences for inner 64, 64' and outer 66, 66' primers (sequences in arrows) for amplification of the double stranded amplicon 62. Also illustrated are sequences for oligonucleotide probes 68, 68' (small case) for use in the fluorescence-based detection method. FIG. 6B illustrates amplification curves (1) where two inner primers (64, 64') are used; (2) where inner and outer primers (64, 66') are used; (3) where inner and outer primers (64', 66) are used; and (4) where two outer primers (64, 64') are used. As can be seen from FIG. 6B, the highest yield ($\Delta R_n$) is achieved when the amplicon is the shortest (1). The yield decreases when the length of the amplicon is increased [(1) vs. (4)]. Amplicons of intermediate length are shown in FIG. 6B to yield intermediate results.

II. Primer and Probe Selection Based On Amplicon Sequence

Several factors influence the selection of the primer and probe sequences to use for a given amplicon. For example, the % GC (percentage of bases in a sequence which are either G or C) should be at least about 20% and less than about of 80%. This acceptable % GC range is quite broad. The reason for this flexibility is that primers and probes which meet the tight $T_m$ ranges defined below can be designed within this broad range of % GC.

The primers should be selected to hybridize to a region which is conserved between different sources of DNA. If the primer selected hybridizes to a polymorphic region, the primer will or will not amplify DNA in the sample depending on the source of the sample. By selecting a primer which hybridizes to a non-polymorphic region, the primer should be able to amplify most samples.

The primers and probes should have less than four contiguous guanines (G). The requirement for no more than 3 contiguous Gs stems from the reduced yield of reactions in which these structures are found. This reduced yield is due to the relatively stable secondary structure created when 4 or more contiguous Gs are found.

III. Probe Selection Based On Amplicon Sequence

In addition to the guidelines of Section II for selecting the amplicon, the following additional guidelines should preferably followed when selecting the probe sequence.

In one embodiment, the probe melting point temperature ($T_m$) is about 3–5° C. greater than the annealing temperature used in the amplification reaction and the primer melting point temperature ($T_m$) is about 2–4° C. less than the annealing temperature. In one embodiment, the annealing temperature is about 60–64° C. and is more preferably about 62° C. When the annealing temperature is about 62° C., the probe melting point temperature is preferably about 65–67° C. and the primer melting point temperature is preferably about 58–60° C.

In another embodiment, the probe melting point temperature ($T_m$) is preferably about 5–10° C. greater than the primer's $T_m$, more preferably about 7° C. greater.

In another embodiment, the probe has a melting point temperature ($T_m$) of about 65–70° C., more preferably about 65–67° C. In this embodiment, the primers preferably have a melting point temperature ($T_m$) of about 55–65° C., more preferably about 58–63° C., most preferably about 58–60° C.

Figure 7:
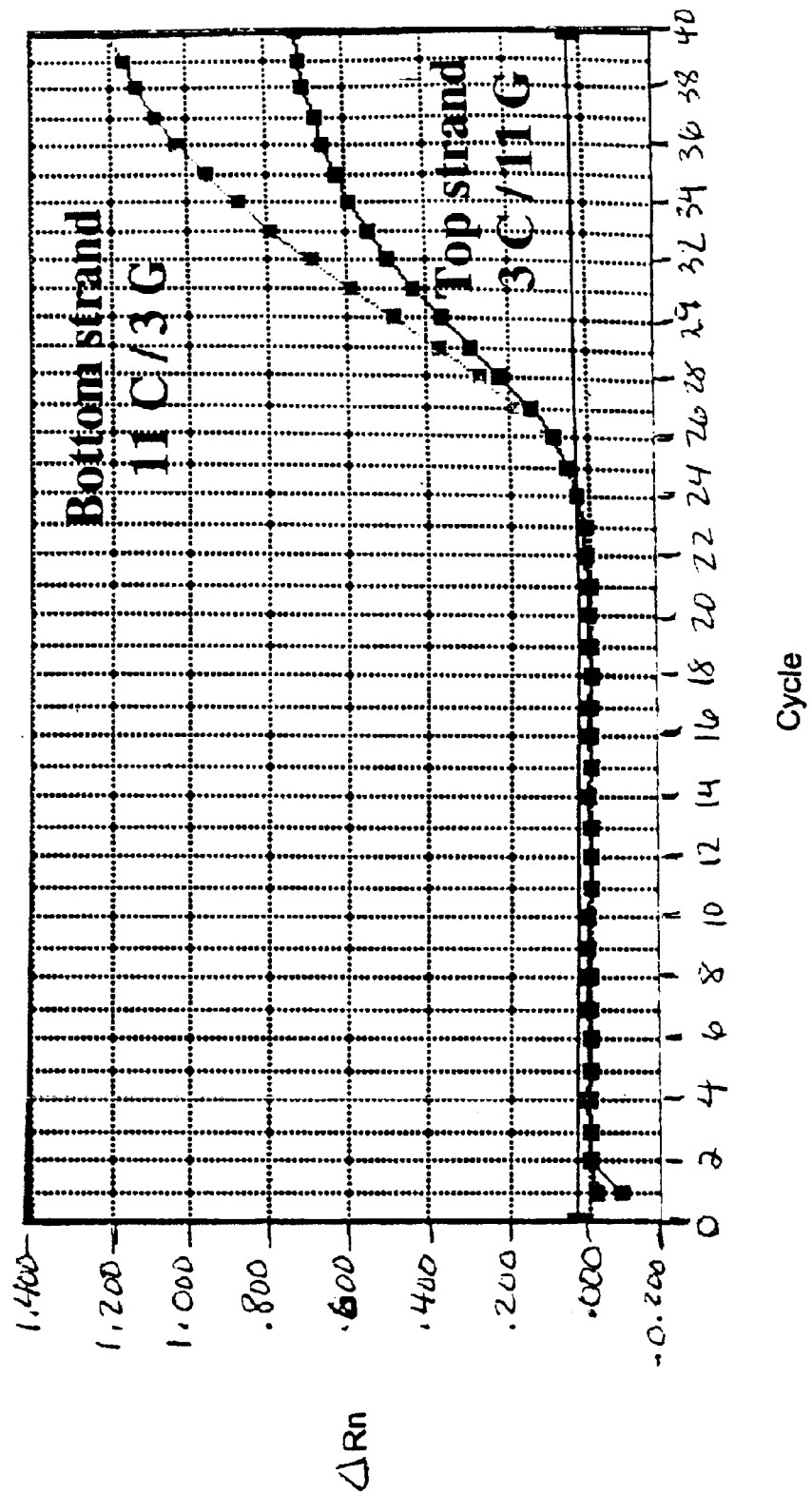
FIG. 7 illustrates that a probe with more Cs than Gs performs better in the 5' nuclease assay.

When selecting which strand of a double stranded target to make the probe complementary to, it is preferred to choose the strand where the resulting probe has more Cs than Gs. This requirement is based on the observation that a probe with more Cs than Gs yields probes which perform better in the 5' nuclease assay, as illustrated in the result shown in FIG. 7.

The probe sequence should not have a guanine (G) at the 5' end. This is because a G adjacent to the fluorescer quenches the fluorescer fluorescence somewhat even after cleavage.

IV. Primer Selection Based on Amplicon Sequence

In addition to the guidelines of Section III above for selecting the amplicon and probe, the following additional guidelines should preferably be followed when selecting the primer sequences.

The primers should be selected after the probe preferences are applied and potential probe sequences are selected. When more than one allelic site is to be amplified by a single primer, as illustrated in FIGS. 4A–4D, the primers are preferably chosen to bracket the probe within the shortest possible amplicon length. The primer sequence is preferably selected to be as close as possible to the probes without overlapping the probes. Amplicons are preferably less than 150 bp in length and more preferably are less than about 100 bp in length. Short amplicons are preferred because shorter sequences increase the probability that the PCR amplification will work. Thus, the robustness of the PCR amplification is most important to the generation of signal from fluorogenic probes. Under the same reaction conditions, shorter amplicons will amplify more efficiently than longer amplicons. The advantage of selecting shorter amplicons is illustrated in FIGS. 6A and 6B with regard to the finding that the use of two inner primers provide the greatest fluorescence yield ($\Delta R_n$).

As also discussed above with regard in FIGS. 6A and 6B, the forward and reverse primers should be as close as possible to the probe without overlapping the probe. The primers preferably have a melting point temperature about 2–4° C. below the annealing temperature used in the amplification. For example, when a preferred annealing temperature of 62° is used, the melting point temperature of the primers is preferably about 58–60° C.

The five nucleotides at the 3' end of the forward and reverse primers should have only one or two guanines (G) or cytosines (C).

The primers should also preferably be chosen with relatively unstable 3' ends in order to reduce non-specific priming. Such primers typically have no more than 2 guanines (G) and cytosines (C) total among the last five 3' end nucleotides. Primers which are less likely to hybridize transiently at their 3' ends are also less likely to be non-specifically extended by DNA polymerase.

How the above guidelines are employed to select the probe and primers to use in the fluorescence monitored amplification reaction will now be illustrated with regard to FIGS. 8–12.

FIGS. 8A and 8B illustrate sequences for Amelogenin X [SEQ. I.D. NO. 1] and Amelogenin Y [SEQ. I.D. NO. 2] respectively from which an amplicon, primers and probe are to be determined. FIG. 9 illustrates a comparison of a portion of Amelogenin X to a portion of Amelogenin Y where the symbol | between the sequences indicates that the two sequences have the same nucleotide at a particular base position and the symbol - between the sequences indicates that the two sequences have a different nucleotide at the particular base position.

FIG. 10 illustrates a portion of Amelogenin X (bases 50–750). with the allelic site to be identified by the 5' nuclease assay illustrated in a bold. FIG. 11 illustrates a bases 251–500 of Amelogenin X illustrated in FIG. 10 along with its complementary (antisense) strand. [SEQ. I.D. NO. 3]. The allelic site to be identified by the 5' nuclease assay is indicated in bold.

A probe complementary to the allelic site of Amelogenin X to be detected is then selected. The probe should be selected to be complementary to either the sense or antisense strand based on which probe has more C's than G's. The length of the probe should be adjusted so that the probe has the desired melting point temperature, preferably between about 65–67° C. A variety of computer programs exist for calculating the melting point temperature of the probe. The following probe is an example of a suitable probe for this allelic site of Amelogenin X based on this selection process: CCAGCAACCMTGATGCCCGTT [SEQ. I.D. NO. 4].

The forward primer to be used in the assay is then selected by searching for primers complementary to a region of Amelogenin X which is closest to the allelic site and uninterrupted by polymorphisms between Amelogenin X and Amelogenin Y. The reverse primer to be used in the assay is then selected by searching for suitable primers which are also uninterrupted by polymorphisms between Amelogenin X and Amelogenin Y. FIG. 12 illustrates the Amelogenin X amplicon selected by this process with the forward and reverse promoters indicated by the arrows. The allelic site is indicated in shadow. The striked-out sequences are sequences where polymorphisms between Amelogenin X and Amelogenin Y are present.

The Amelogenin Y probe is then selected to have a melting point temperature within the same range as Amelogenin X, preferably between about 65–67° C. as stated above. The following probe is an example of a suitable probe for this allelic site of Amelogenin Y based on this selection process: CCAGCMGCACTGATGCCTGTTC [SEQ. I.D. NO. 5].

B. Conditions For Running 5' Nuclease Assay

The probe and primer design constraints outlined above provide reproducible physicochemical parameters for the target amplicons. Amplifications for all amplicons selected through this process can be run under the same reaction mixture formulation and thermocycler parameters. Table 1 provides ranges for a preferred reaction mixture formulation as well as a specific example of a reaction mixture formulation that is preferably used in the assay. The reaction mixture formulations outlined in Table 1 has been found to be stable over 90 days at 2–8° C. Reagents in the TaqMan PCR Core Reagent Kit (Part No. N8080228) and 20% Glycerol (Part No. 402929) sold by Applied Biosystems—Perkin Elmer are preferably used to prepare the reaction mixture.

Glycerol is used in the reaction mixture to help melt GC base pairs. Gelatin and TWEEN 20 are used to stabilize ROX fluorescence which otherwise decreases over time.

AMPLITAQ™ Gold is used as the polymerase as part of a hot start method because AMPLITAQ™ Gold does not operate until activated by incubation at 95° C. By using the hot start method, improved specificity, sensitivity and product yield is achieved. The hot start method and its advantages are described in Birch, et al., *Nature,* 381: 445–446 (1996).

AmpErase UNG™ is used in combination with AMPLITAQ™ Gold. AmpErase UNG™ recognizes U in DNA and takes U out of the amplicons, leaving a phosphate backbone. When the reaction temperature is raised to 95° C. for AMPLITAQ™ Gold, the phosphate backbone where the U's have been removed falls apart. This serves to prevent amplification of contaminating amplicons from previous amplifications.

The relatively high (5mM) final concentration of $MgCl_2$ in the reaction mixture follows a strategy of requiring all generic reagents to be present in excess for this reaction. An inherent property of 5' nuclease assays is that for a signal to be generated the probe must be hybridized to the extension complex during the PCR. Using a high concentration of $Mg^{+2}$ shifts the hybridization equilibrium toward the probe being hybridized. The result is that the probe hybridization is much more stable and the reactions more robust and reproducible.

TABLE 1

2X Reaction Mix

| Reagent | Volume (ml)* | Concentration | Range |
|---|---|---|---|
| glycerol | 8.00 | 16% | 14–18% |
| 2% gelatin | 2.50 | 0.1% | 0.08–0.12% |
| tween 20 | 0.01 | 0.02% | 0.01–0.03% |
| tris 1.0 M, pH 8.0 | 5.00 | 100 mM | 50–150 mM |
| Mg C12 1 M | 0.50 | 10 mM | 9–11 mM |
| dATP 0.1 M | 0.20 | 400 uM | 350–450 uM |
| dCTP 0.1 M | 0.20 | 400 uM | 350–450 uM |
| deaza dGTP 10 mM | 2.00 | 400 uM | 350–450 uM |
| dUTP 0.1 M | 0.40 | 800 uM | 700–900 uM |
| AmpliTaq Gold 5 U/uL | 1.0 | 0.10 U/uL | .09–.11 U/uL |
| AmpErase UNG 1 U/uL | 1.0 | 0.02 U/uL | .01–.03 U/uL |
| Passive Reference 30 uM | 0.20 | 120 nM | 114–126 nM |
| milliQ water | 28.99 | | |
| TOTAL | 50 ml | | |

*For a 50 mL aliquot

Table 2 outlines the preferred Thermal Cycle Parameter Settings for these amplification reactions. More than one type of target quantitation test may be run in a 96-well plate, since all tests share the same thermocycler parameter settings.

TABLE 2

TIMES AND TEMPERATURES

| INITIAL STEPS | | EACH OF 40 CYCLES | |
|---|---|---|---|
| HOLD | HOLD | MELT | ANNEAL/EXTEND |
| 2 min @50° C. | 10 min. @95° C. | 15 sec. @95° C. | 1 min. @62° C. |

C. Optimization of Primer and Probe Concentrations

Only primer and probe concentration optimizations are required for tests run with primers, probes, reaction mixture and thermocycler parameters as outlined here. The purpose of the primer concentration optimizations is to obtain an effective $T_m$ that results in optimum PCR and maximum end point values. The purpose of the probe concentration optimizations is to reach the minimum probe concentrations required for optimum 5' nuclease performance and maximum fluorescent signal. After the primer and probe concentrations have been determined, the concentration for each primer is independently optimized to determine the minimum primer concentration which yields maximum end point values. The concentration for each probe is optimized for each target to determine the minimum probe concentration that yields the best yield and $C_T$.

A template with the target sequence is required for the optimization. This template may be genomic DNA or cDNA generated from a reverse transcription reaction, or a plasmid which contains the target sequence.

D. Determination of Primer and Probe Concentrations

In order to determine the concentrations of the probes and primers, measure the absorbance at 260 nm of a 1:100 dilution of each oligonucleotide in TE buffer. Then calculate the oligonucleotide concentration in $\mu$M using the method shown below in Table 3.

TABLE 3

Example of an extinction coefficient calculation for a FAM-labeled probe.

| Chromophore | Extinction Coefficient | Number | Extinction Coefficient Contribution |
|---|---|---|---|
| A | 15,200 | 1 | 15,200 |
| C | 7,050 | 6 | 42,300 |
| G | 12,010 | 5 | 60,050 |
| T | 8,400 | 6 | 50,400 |
| FAM | 20,958 | 1 | 20,958 |
| TAMRA | 31,980 | 1 | 31,980 |
| TET | 16,255 | 0 | — |
| TOTAL | — | — | 220,888 |

Absorbance = extinction coefficient × path length × concentration/100.
In this case, 0.13 = 221,000 $M^{-1}$ $cm^{-1}$ × 0.3 cm × C/100, or C = 196 $\mu$M.

E. Optimization of Primer Concentrations

Primer concentrations may be optimized at the 62° C. elongation temperature defined above. The forward and reverse primers are cooptimized by running the wells defined by the 3×3 matrix shown in Table 4 at a 100 nM probe concentration. A minimum of 4 replicate wells is run for each of the 9 conditions defined by this matrix. The primer concentration ranges (50–900 nM) in this matrix correspond to an effective $T_m$ range of +/−2° C. around the nominal $T_m$ for these primers.

Table 5 shows the matrix to use in the optimization of primer concentrations. This matrix should be run with the reaction mixture whose composition is described in Table 1 and the Thermal Cycle Parameter Settings outlined in Table 2. A probe concentration of 100 nM may be used for the primer concentration optimization associated with this matrix. The best combination of primer concentrations will be the one resulting in the lowest threshold cycle ($C_T$) and highest end point ($R_n$) values.

TABLE 4

| Forward | Reverse Primer (nM) | | |
|---|---|---|---|
| Primer (nM) | 50 | 300 | 900 |
| 50 | 50/50 | 50/300 | 50/900 |
| 300 | 300/50 | 300/300 | 300/900 |
| 900 | 900/50 | 900/300 | 900/900 |

F. Optimization of Probe Concentrations

Probe concentrations are optimized at the 62° C. elongation temperature and optimum forward and reverse primer concentrations defined above. When a single probe is used, its concentration is optimized by running wells at 25 nM intervals between 25 and 225 nM. The purpose of this optimization is to choose the minimum probe concentration yielding the maximum $R_n$ and minimum $C_r$. A minimum of 4 replicate wells are run for each of the 9 conditions defined by this matrix. Probe concentrations need to be shown not to be limiting. In a quantitative application, the signal-to-noise is optimized at a maximum.

Table 5 shows the matrix to use in the optimization of probe concentrations. This matrix should be run with the reaction mixture from Table 1 the Thermal Cycle Parameter Settings from Table 2, and the optimum forward and reverse primer concentrations from the primer concentration optimization matrix.

TABLE 5

| Allele 1 Probe (nM) | Allele 2 Probe (nM) | | |
|---|---|---|---|
| | 50 | 150 | 250 |
| 50 | 50/50 | 50/150 | 50/250 |
| 150 | 150/50 | 150/150 | 150/250 |
| 250 | 250/50 | 250/150 | 250/250 |

7. Synthesis of Allelic Probes

Oligonucleotide probes for use in the 5' nuclease assay of the present invention can be synthesized by a number of approaches, e.g., is Ozaki et al., Nucleic Acids Research, 20: 5205–5214 (1992); Agrawal et al., Nucleic Acids Research, 18: 5419–5423 (1990); or the like. The oligonucleotide probes of the invention are conveniently synthesized on an automated DNA synthesizer, e.g., an Applied Biosystems, Inc. (Foster City, Calif.) model 392 or 394 DNA/RNA Synthesizer, using standard chemistries, such as phosphoramidite chemistry, e.g., disclosed in the following references: Beaucage and Iyer, Tetrahedron, 48: 2223–2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the hybridization efficiencies of the resulting oligonucleotides and/or cleavage efficiency of the nuclease employed are not adversely affected.

Preferably, the oligonucleotide probe is in the range of 15–60 nucleotides in length. More preferably, the oligonucleotide probe is in the range of 18–30 nucleotides in length. The precise sequence and length of an oligonucleotide probe of the invention depends in part on the nature of the target oligonucleotide sequence to which it binds. The binding location and length may be varied to achieve appropriate annealing and melting properties for a particular embodiment. Guidance for making such design choices can be found in many of the above-cited references describing the 5' nuclease assays.

Preferably, the 3' terminal nucleotide of the oligonucleotide probe is blocked or rendered incapable of extension by a nucleic acid polymerase. Such blocking is conveniently carried out by the attachment of a reporter or quencher molecule to the terminal 3' carbon of the oligonucleotide probe by a linking moiety.

8. Selection of Fluorescer and Quencher Dyes

Preferably, the fluorescers are fluorescent organic dyes derivatized for attachment to the terminal 3' carbon or terminal 5' carbon of the probe via a linking moiety. Preferably, quencher molecules are also organic dyes, which may or may not be fluorescent, depending on the embodiment of the invention. For example, in a preferred embodiment of the invention, the quencher molecule is fluorescent. Generally whether the quencher molecule is fluorescent or simply releases the transferred energy from the fluorescer by non-radiative decay, the absorption band of the quencher should substantially overlap the fluorescent emission band of the fluorescer. Non-fluorescent quencher molecules that absorb energy from excited fluorescers, but which do not release the energy radiatively, are referred to in the application as chromogenic molecules.

There is a great deal of practical guidance available in the literature for selecting appropriate fluorescer-quencher pairs for particular probes, as amplified by the following references: Clegg (cited above); Wu et al. (cited above); Pesce et al., editors, Fluorescence Spectroscopy (Marcel Dekker, New York, 1971); White et al., Fluorescence Analysis: A Practical Approach (Marcel Dekker, New York, 1970); and the like. The literature also includes references providing exhaustive lists of fluorescent and chromogenic molecules and their relevant optical properties for choosing reporter-quencher pairs, e.g., Beriman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Haugland (cited above); Ullman et al., U.S. Pat. No. 3,996,345; Khanna et al., U.S. Pat. No. 4,351,760; and the like.

Exemplary fluorescer-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Several particular classes of dyes that may be used are the energy transfer fluorescent dyes described in "ENERGY TRANSFER DYES WITH ENHANCED FLUORESCENCE," application Ser. No. 08/726.462; "ENERGY TRANSFER DYES WITH ENHANCED FLUORESCENCE," application Ser. No. 08/642,330; and 4,7-dichlororhodamine dyes described in U.S. application Ser. No. 08/672,196; entitled: "4,7-DICHLORORHODAMINE DYES" which are incorporated herein by reference. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

Preferably, fluorescer and quencher molecules are selected from fluorescein and rhodamine dyes. These dyes and appropriate linking methodologies for attachment to oligonucleotides are described in many references, e.g., Khanna et al. (cited above); Marshall, Histochemical J., 7: 299–303 (1975); Menchen et al., U.S. Pat. No. 5,188,934; Menchen et al., European Patent Application 87310256.0; and Bergot et al., International Application PCT/US90/05565. The latter four documents are hereby incorporated by reference.

There are many linking moieties and methodologies for attaching fluorescer or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305–5321 (1987) (3' thiol group on oligonucleotide); Sharma et al., Nucleic Acids Research, 19: 3019 (1991) (3' sulfhydryl); Giusti et al., PCR Methods and Applications, 2: 223–227

(1993) and Fung et al., U.S. Pat. No. 4,757,141(5' phosphoamino group via Aminolink™ ‖ available from Applied Biosystems, Foster City, Calif.) Stabinsky, U.S. Pat. No. 4,739,044 (3' aminoalkylphosphoryl group); Agrawal et al., Tetrahedron Letters, 31: 1543–1546 (1990) (attachment via phosphoramidate linkages); Sproat et al., Nucleic Acids Research, 15: 4837 (1987) (5' mercapto group); Nelson et al., Nucleic Acids Research, 17: 7187–7194 (1989) (3' amino group); and the like.

Preferably, commercially available linking moieties are employed that can be attached to an oligonucleotide during synthesis, e.g., available from Clontech Laboratories (Palo Alto, Calif.).

Rhodamine and fluorescein dyes are also conveniently attached to the 5' hydroxyl of an oligonucleotide at the conclusion of solid phase synthesis by way of dyes derivatized with a phosphoramidite moiety, e.g., Woo et al., U.S. Pat. No. 5,231,191; and Hobbs, Jr., U.S. Pat. No. 4,997,928.

9. Determining Fluorescence Signatures for Apoe Allelic Controls

Apolipoprotein (apo) E plays a central role in lipoprotein metabolism by mediating interactions between lipoproteins and liporeceptors. Three common variants of apoE have been identiffied by isoelectric focusing and have been designated E2, E3 and E4. Genetic variation in apoE affects serum cholesterol levels, propensity to coronary artery disease, and propensity to develop late onset Alzheimer's disease.

The common protein variants E2, E3, and E4 are encoded by three alleles of the apoE gene termed $\epsilon2$, $\epsilon3$, and $\epsilon4$. These alleles are illustrated in Table 6. As illustrated, the apoE alleles differ by single base substitutions in two codons, 112 and 158. Thus, genotyping of apoE requires determination of base identity at two distinct allelic sites in the apoE gene.

TABLE 6

|  | Codon 112 | Codon 158 |
| --- | --- | --- |
| $\epsilon2$ | T | T |
| $\epsilon3$ | T | C |
| $\epsilon4$ | CGC | CGC |
| E2 | Arg | Arg |
| E3 | Cys | Arg |
| E4 | Cys | Cys |

The two allelic sites are close enough so they can be amplified as a single apoE amplicon. However, the sites are too far apart to be assayed by a single probe. Gel methods such as sequencing or restriction digests of PCR products can assay both polymorphic sites in a single reaction product, but they require the use of labor intensive gels. The non-gel methods described to date assay each polymorphic site separately so that two reactions are required to determine an individuals apoE genotype.

Using the 5' nuclease assay according to the present invention, it is possible to determine the genotype at both allelic sites in a single reaction. This approach is much faster than previous approaches to genotyping genes having two or more allelic sites, such as the apoE gene.

The probes used in the 5' nuclease assay to distinguish the various apoE alleles are:

```
Codon 112
    CGGCCGCACACGTCCTCCp            AE112T1    [SEQ. ID. No.6]
    TET-CGGCCGCGCACGTCCTCCTC-TAMRA AE112CT2   [SEQ. ID. No.7]

Codon 158
    FAM-CACTGCCAGGCACTTCTGCA-TAMRA AE158TF1   [SEQ. ID. No.8]
    JOE-CACTGCCAGGCGCTTCTGCAG-TAMRA AE158CJ2  [SEQ. ID. No.9]
```

The bolded base is complementary to the polymorphic T or C at each codon.

At codon 112, AE112T1 hybridizes to the $\epsilon2$ and $\epsilon3$ alleles which each include A at codon 112. Since AE112T1 does not include a fluorescer, samples of $\epsilon2$ and $\epsilon3$ do not produce a signal for the 112 codon allele.

At codon 112, AE112T2 hybridizes to the $\epsilon4$ allele which include G at codon 112. Since AE112T2 includes TET as the fluorescer, samples of $\epsilon4$ produce a TET signal for the 112 codon allele.

At codon 158, AE158TF1 hybridizes to the $\epsilon2$ allele which includes A at codon 158. Since AE 158TF1 includes FAM as the fluorescer, samples of $\epsilon2$ produce a FAM signal for the 158 codon allele.

At codon 158, AE158CJ2 hybridizes to the $\epsilon3$ and $\epsilon4$ alleles which include G at codon 158. Since AE158CJ2 includes JOE as the fluorescer, samples of $\epsilon3$ and $\epsilon4$ produce a JOE signal for the 158 codon allele. Table 7 summarizes the fluorescence signals that would be expected for the various apoE alleles. As can be seen from Table 7, a distinctive spectrum can be expected for each allelic variant, thus allowing discrimination of the alleles and detection of heterozygote combinations.

TABLE 7

|  | FAM | TET | JOE |
| --- | --- | --- | --- |
| $\epsilon2$ | X |  |  |
| $\epsilon3$ |  |  | X |
| $\epsilon4$ |  | X | X |

Codons 112 and 158 were amplified as part of a 273 base amplicon using the following primers:

```
                                       [SEQ. ID. No. 10];
ApoE-F1  ACGCGGGCACGGCTGTC (forward primer)
                                       [SEQ. ID. No. 11].
ApoE-R1  CTCGCGGATGGCGCTGA (reverse primer)
```

The specific reaction mixture shown in Table 1 and the reaction conditions shown in Table 2 were used to perform the amplification of the apoE alleles.

Figure 13:
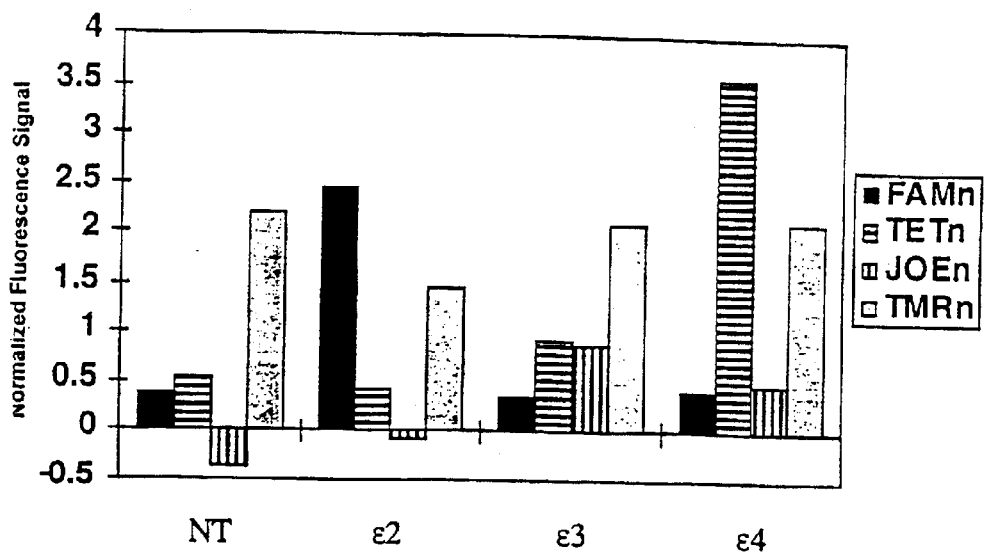
FIG. 13 illustrates the normalized relative contributions of FAM, TET, JOE, and TAMRA to spectra derived from performing the above-described 5' nuclease assay on apoE alleles $\epsilon 2$, $\epsilon 3$, and $\epsilon 4$ and on a sample with no template (NT).

After amplification, the fluorescence of each reaction was measured on an ABI Prism 7200 or 7700. The software on the instrument uses a reference library of the pure dye spectra as well as logic for determining the fluorescence contribution of the different fluorophores to the spectrum by multicomponenting analysis. Present in the reaction are the 3 fluorescers (TET, FAM, and JOE), the quencher (TAMRA), and a passive internal reference (ROX). Once the relative contributions of FAM, TET, JOE, and TAMRA are determined, the ROX signal is used to normalize the other signals by dividing the FAM, TET, JOE, and TAMRA signals by the ROX signal. FIG. 13 illustrates the normalized relative contributions of FAM, TET, JOE, and TAMRA to spectra derived from performing the above-described 5' nuclease assay on apoE alleles ε2, ε3, and ε4 and on a sample with no template (NT). These are the fluorescence signatures for the different alleles.

As can be seen from fluorescence signatures shown in FIG. 13, the determination of the relative contributions of FAM, TET, JOE, and TAMRA to the fluorescence signal can result in some seemingly illogical results which prevent the fluorescence data from being read directly in order to determine a genotype of an unknown. For example, the JOE signal is shown to be negative for samples with the ε2, allele and with no template (NT). Further, the ε3 allele has a stronger TET signal than a JOE signal despite the fact that one would expect the ε3 allele to only have a JOE signal. These results are due to variations in the extinction coefficients of the different fluorescers, competition between allelic probes, and imprecisions in the multicomponenting analysis logic. Instead of being used to determine genotypes directly, the normalized relative fluorescence contributions shown in FIG. 13 are used as fluorescence signatures which can be compared to signatures derived from unknown samples in order to identify the genotypes of the unknown samples.

10. Genotyping Apoe Unknowns

A plate was run containing 3 NT controls, 3 ε2 controls, 3 ε3 controls, 3 ε4 controls, and 84 unknowns samples according to the assay described in Section 9. Each unknown reaction contained 50 ng genomic DNA from one of 84 human individuals. Reaction volume was 25 μl. After performing the 5' nuclease assay and measuring the fluorescence, normalized fluorescence signatures were determined for the each sample. By comparing to the NT controls to the fluorescence of the unknown samples, three unknowns were determined to have not undergone significant amplification. Further analysis of these samples was discontinued.

The average of the fluorescence signatures of the series of control samples and NT samples were used to construct a 4×4 matrix as shown below.

$$[NT\ \varepsilon2\ \varepsilon3\ \varepsilon4] = [FAM_n\ TET_n\ JOE_n\ TMR_n] \times \begin{bmatrix} FAM_{n,NT} & TET_{n,NT} & JOE_{n,NT} & TMR_{n,NT} \\ FAM_{n,\varepsilon2} & TET_{n,\varepsilon2} & JOE_{n,\varepsilon2} & TMR_{n,\varepsilon2} \\ FAM_{n,\varepsilon3} & TET_{n,\varepsilon3} & JOE_{n,\varepsilon3} & TMR_{n,\varepsilon3} \\ FAM_{n,\varepsilon4} & TET_{n,\varepsilon4} & JOE_{n,\varepsilon4} & TMR_{n,\varepsilon4} \end{bmatrix}^{-1}$$

This matrix was then used to calculate NT, ε2, ε3, and ε4 values for each unknown.

Figure 14:
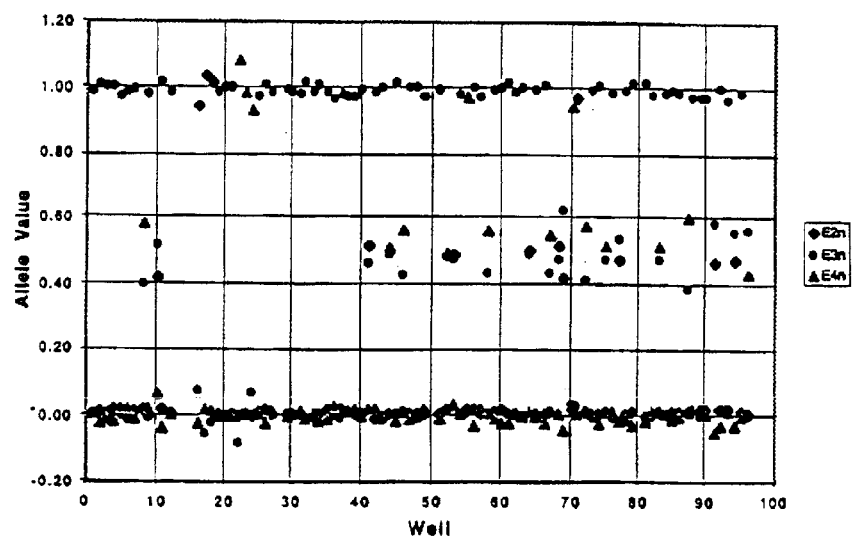
FIG. 14 illustrates a plot of allele value versus well for the ApoE genotyped samples.

FIG. 14 illustrates a plot of allele value versus well for the 84 genotyped samples. This plot is obtained by removing the NT contribution to the spectra and then renormalizing the signature without NT. This enables one to have 1, 0.5, or 0 allele values where each allele has an allele value of 0.5. It can be seen that the allele values cluster around 0.0, 0.5, and 1.0 as would be expected. The most common genotype is an ε3 homozygote. These individuals have an ε3 value of approximately 1.0 and ε2 and ε4 values of approximately 0.

Figure 15:
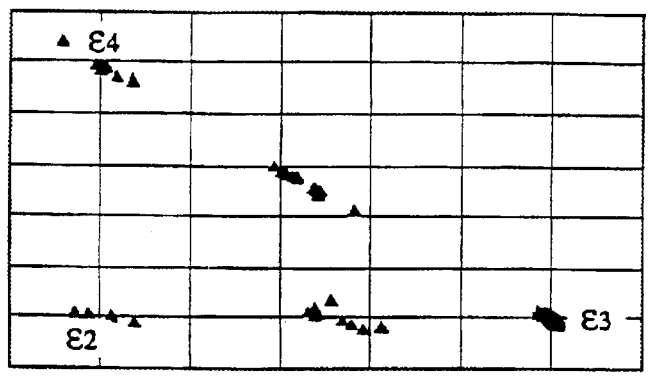
FIG. 15 illustrates a scatter plot diagram of $\epsilon 3$ versus $\epsilon 4$ for the data shown in FIG. 14.

Another way of viewing the data shown in FIG. 14 is as a scatter plot diagram of ε3 value versus ε4 value shown in FIG. 15. Because of the normalization, any individual which has a value of 0 for both ε3 and ε4 must be an ε2 homozygote.

As shown in FIGS. 14 and 15, the 84 samples where found to have the following ApoE genotypes:

1 ε2 homozygote
57 ε3 homozygote
3 ε4 homozygote
9 ε2/ε3 heterozygote
11 ε3/ε4 heterozygote
3 non amplification These results demonstrate the ability of the assay to determine apoE genotypes for a series of samples rapidly and accurately. This assay can be used as a diagnostic tool for assessing the risk for coronary artery disease and/or late-onset Alzheimer's disease.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A kit for identifying in a single 5' nuclease assay which alleles at multiple different allelic sites are present in a sample of DNA, the kit comprising:

a first set of oligonucleotide probes comprising first and second oligonucleotide probes for detecting which alleles are present at a first allelic site by single 5' nuclease assay, the first and second oligonucleotide probes being designed to distinguish between at least two alleles at the first allelic site which differ from each other by at least one base position, wherein the first set of oligonucleotide probes is digestible by a 5' to 3' nuclease, and does not self-hybridize;

a second set of oligonucleotide probes comprising third and fourth oligonucleotide probes for detecting which alleles are present at a second, different allelic site by the single 5' nuclease assay, the third and fourth oligonucleotide probes being designed to distinguish between at least two alleles at the second allelic site which differ from each other by at least one base position, wherein the second set of oligonucleotide probes is digestible by a 5' to 3' nuclease, and does not self-hybridize; and a first primer that is capable of hybridizing to a sequence in the first allelic site 3' relative to where the probes of the first set hybridize to the first allelic site and a second primer that is capable of hybridizing to a sequence in the second allelic site 3' relative to where the probes of the second set hybridize to the second allelic site;

wherein one of the first, second, third and fourth oligonucleotide probes lacks a fluorescer and the other three probes each include a different fluorescer, the three different fluorescers being selected such that the first and second sets of oligonucleotide probes can be used to determine which alleles are present at the first and second allelic sites in the single 5' nuclease assay, and each of the three fluorescer-containing probes with a fluorescer includes a same quencher to quench the fluorescence of the fluorescer.

2. A kit according to claim 1, wherein all of the probes have a melting point temperature that is about 3–5° C. greater than an annealing temperature used in the amplification, and the primers' melting point temperatures are about 2–4° C. less than the annealing temperature.

3. A kit according to claim 2, wherein the primers have a melting point temperature of about 58–60° C.

4. A kit according to claim 1, wherein all of the probes have a melting point temperature about 7° C. greater than the melting point temperature of the primers.

5. A kit according to claim 1, wherein the % GC of all the probes are at least about 20% and less than about 80%.

6. A kit according to claim 1, wherein none of the probes have four or more contiguous guanines.

7. A kit according to claim 1, wherein all of the probes have a melting point temperature about 65–67° C.

8. A kit according to claim 1, wherein the three different fluorescers on the oligonucleotide probes are capable of being excited at the same wavelength.

9. A kit according to claim 1, wherein the oligonucleotide probes are in a non-hairpin, single stranded form when not hybridized to a sequence.

10. A kit for identifying in a single 5' nuclease assay which alleles at multiple different allelic sites are present in a sample of DNA, the kit comprising:

a first set of oligonucleotide probes comprising first and second oligonucleotide probes for detecting which alleles are present at a first allelic site by a single 5' nuclease assay, the first and second oligonucleotide probes being designed to distinguish between at least two alleles at the first allelic site which differ from each other by at least one base position, wherein the first set of oligonucleotide probes is digestible by a 5' to 3' nuclease, and does not self-hybridize;

a second set of oligonucleotide probes comprising third and fourth oligonucleotide probes for detecting which alleles are present at a second, different allelic site by the single 5' nuclease assay, the third and fourth oligonucleotide probes being designed to distinguish between at least two alleles at the second allelic site which differ from each other by at least one base position, wherein the second set of oligonucleotide probes is digestible by a 5' to 3' nuclease, and does not self-hybridize; and a first primer that is capable of hybridizing to a sequence in the first allelic site 3' relative to where the probes of the first set hybridize to the first allelic site and a second primer that is capable of hybridizing to a sequence in the second allelic site 3' relative to where the probes of the second set hybridize to the second allelic site;

wherein one of the first, second, third and fourth oligonucleotide probes lacks a fluorescer and the other three probes comprise at least 15 nucleotides and include a different fluorescer, the three different fluorescers being selected such that the first and second sets of oligonucleotide probes can be used to determine which alleles are present at the first and second allelic sites in the single 5' nuclease assay, and each of the three fluorescer-containing probes with a fluorescer includes a same quencher to quench the fluorescence of the fluorescer.

11. A kit according to claim 10, wherein all of the probes have a melting point temperature that is about 3–5° C. greater than an annealing temperature used in the amplification, and the primers' melting point temperatures are about 2–4° C. less than the annealing temperature.

12. A kit according to claim 10, wherein the primers have a melting point temperature of about 58–60° C.

13. A kit according to claim 10, wherein all of the probes have a melting point temperature about 7° C. greater than the melting point of the primers.

14. A kit according to claim 10, wherein the % GC of all the probes are at least about 20% and less than about 80%.

15. A kit according to claim 10, wherein none of the probes have four or more contiguous guanines.

16. A kit according to claim 10, wherein all of the probes have a melting point temperature of about 65–67° C.

17. A kit according to claim 10, wherein the three different fluorescers on the oligonucleotide probes are capable of being excited at a same wavelength.

18. A kit according to claim 10, wherein the oligonucleotide probes are in a non-hairpin, single stranded form when not hybridized to a sequence.

19. A kit according to claim 1, wherein all of the probes have a melting point temperature about 5–10° C. greater than the melting point temperature of the primers.

20. A kit according to claim 10, wherein all of the probes have a melting point temperature about 5–10° C. greater than the melting point temperature of the primers.

21. A kit for identifying in a single 5' nuclease assay which alleles at multiple different allelic sites are present in a sample DNA, the kit comprising:

a first set of oligonucleotide probes comprising first and second oligonucleotide probes for detecting which alleles are present at a first allelic site by single 5' nuclease assay, the first and second oligonucleotide probes being designed to distinguish between at least two alleles at the first allelic site which differ from each other by at least one base position, wherein the first set of oligonucleotide probes is digestible by a 5' to 3' nuclease, and does not self-hybridize;

a second set of oligonucleotide probes comprising third and fourth oligonucleotide probes for detecting which alleles are present at a second, different allelic site by the single 5' nuclease assay, the third and fourth oligonucleotide probes being designed to distinguish between at least two alleles at the second allelic site which differ from each other by at least one base position, wherein the second set of oligonucleotide probes is digestible by a 5' to 3' nuclease, and does not self-hybridize;

a first primer that is capable of hybridizing to a sequence in the first allelic site 3' relative to where the probes of the first set hybridize to the first allelic site and a second primer that is capable of hybridizing to a sequence in the second allelic site 3' relative to where the probes of the second set hybridize to the second allelic site; and a polymerase having 5' to 3' nuclease activity;

wherein one of the first, second, third and fourth oligonucleotide probes lacks a fluorescer and the other three probes comprise at least 15 nucleotides and include a different fluorescer, the three different fluorescers being selected such that the first and second sets of oligonucleotide probes can be used to determine which alleles are present at the first and second allelic sites in the single 5' nuclease assay, each of the three fluorescer-containing probes with a fluorescer includes a same quencher to quench the fluorescence of the fluorescer, and each quencher and each fluorescer are at opposite ends of each probe.

22. A kit for identifying in a single 5' nuclease assay which alleles at multiple different allelic sites are present in a sample of DNA, the kit comprising:

a first set of oligonucleotide probes comprising first and second oligonucleotide probes for detecting which alleles are present at a first allelic site by single 5' nuclease assay, the first and second oligonucleotide probes being designed to distinguish between at least two alleles at the first allelic site which differ from each by at least one base position;

a second set of oligonucleotide probes comprising third and fourth oligonucleotide probes for detecting which alleles are present at a second, different allelic site by the single 5' nuclease assay, the third and fourth oligonucleotide probes being designed to distinguish between at least two alleles at the second allelic site which differ from each other by at least one base position, wherein the first and second sets of oligonucleotide probes are capable of being excited at the same wavelength; and a first primer that is capable of hybridizing to a sequence in the first allelic site 3' relative to where the probes of the first set hybridize to the first allelic site and a second primer that is capable of hybridizing to a sequence in the second allelic site 3' relative to where the probes of the second set hybridize to the second allelic site;

wherein one of the first, second, third and fourth oligonucleotide probes lacks a fluorescer and the other three probes comprise at least 15 nucleotides and include a different fluorescer, the fluorescers being selected such that the first and second sets of oligonucleotide probes can be used to determine which alleles are present at the first and second allelic sites in the single 5' nuclease assay, each of the three fluorescer-containing probes with a fluorescer including a same quencher to quench the fluorescence of the fluorescer, and each quencher and each fluorescer are at opposite ends of each probe.

* * * * *

SEQUENCE LISTING

<160> NUMBER OF SEQ ID NOS: 11

<210> SEQ ID NO 1
<211> LENGTH: 793
<212> TYPE: DNA
<213> ORGANISM: Homo sapiens

<400> SEQUENCE: 1

```
aaaggatcaa gcatccctga gtttcaaaca gaaacttgca ctgaatacat tcaaagaacc      60
atcaagaaat ggggacctgg attttatttg cctgcctcct gggagcagct tttgccatgc     120
ctctaccacc tcatcctggg caccctggtt atatcaactt cagctatgag gtgcttaccc     180
ctttgaagtg gtaccagagc ataaggccac cgtacccttc ctatggttac gagcccatgg     240
```

| | |
|---|---:|
| gtggatggct gcaccaccaa atcatccccg tgctgtccca acagcacccc ccgactcaca | 300 |
| ccctgcagcc tcatcaccac atcccagtgg tgccagctca gcagcccgtg atcccccagc | 360 |
| aaccaatgat gcccgttcct ggccaacact ccatgactcc aatccaacac caccagccaa | 420 |
| acctccctcc gcccgcccag cagccctacc agccccagcc tgttcagcca cagcctcacc | 480 |
| agcccatgca gccccagcca cctgtgcacc ccatgcagcc cctgccgcca cagccacctc | 540 |
| tgcctccgat gttccccatg cagcccctgc tcccatgct tcctgatctg actctggaag | 600 |
| cttggccatc aacagacaag accaagcggg aggaagtgga ttaaaagatc agaagatgag | 660 |
| aggggaatga atacttcaga tgctttcagg agtgacacaa gaacacaatg atttttgctt | 720 |
| ataatcactt tacttagcaa attctgtaac taaaaaagta ccattagcag acaataaaat | 780 |
| gcattaaaaa tca | 793 |

<210> SEQ ID NO 2
<211> LENGTH: 802
<212> TYPE: DNA
<213> ORGANISM: Homo sapiens

<400> SEQUENCE: 2

| | |
|---|---:|
| agaggaccaa gcctccctgt gtagcacaaa gaaagtttct ctgaatatat ttaaagaacc | 60 |
| atcaagaaat ggggacctgg attttgtttg cctgccttgt gggagcagct tttgccatgc | 120 |
| ctctaccacc tcatcctggg caccctggtt atatcaactt cagctatgag gtgctcaccc | 180 |
| cttttgaagtg gtaccagagc atgataagac caccatactc ttcctatggt tacgagccca | 240 |
| tgggtggatg gctgcaccac caaatcatcc ccgtggtgtc ccaacagcac cccctgactc | 300 |
| acaccctgca gtctcatcac acatcccag tggtgccagc tcagcagccc agggtccgcc | 360 |
| agcaagcact gatgcctgtt cctggccagc aatccatgac tccaacccaa caccatcagc | 420 |
| caaacctccc tctgcctgcc cagcagccct ccagcccca gcctgttcag ccacagcctc | 480 |
| accagcccat gcagccccag ccacctgtgc aacccatgca gcccctgctg ccacagccac | 540 |
| ctctgcctcc aatgttcccc ctgcggcccc tgccccccat acttcctgat ctgcatctgg | 600 |
| aagcttggcc agcaacagac aagaccaagc aggaggaagt ggattaaaag accagaatat | 660 |
| gagacaggaa ctgaagtaaa cactttagtt gctttcaggg atgacacaag cacacaatga | 720 |
| tttttgctta caatcactta acttagcaaa ttctgtaact aaaaatgtac caatagtaga | 780 |
| caataaaatg ttttaaaaat ca | 802 |

<210> SEQ ID NO 3
<211> LENGTH: 500
<212> TYPE: DNA
<213> ORGANISM: Homo sapiens

<400> SEQUENCE: 3

| | |
|---|---:|
| aaaggatcaa gcatccctga gtttcaaaca gaaacttgca ctgaatacat tcaaagaacc | 60 |
| atcaagaaat ggggacctgg attttatttg cctgcctcct gggagcagct tttgccatgc | 120 |
| ctctaccacc tcatcctggg caccctggtt atatcaactt cagctatgag gtgcttaccc | 180 |
| cttttgaagtg gtaccagagc ataaggccac cgtacccttc ctatggttac gagcccatgg | 240 |
| gtggatggct gcaccaccaa atcatcccc tgctgtccca acagcacccc ccgactcaca | 300 |
| ccctgcagcc tcatcaccac atcccagtgg tgccagctca gcagcccgtg atcccccagc | 360 |
| aaccaatgat gcccgttcct ggccaacact ccatgactcc aatccaacac caccagccaa | 420 |
| acctccctcc gcccgcccag cagccctacc agccccagcc tgttcagcca cagcctcacc | 480 |

```
agcccatgca gccccagcca                                              500

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
ccagcaacca atgatgcccg tt                                           22

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
ccagcaagca ctgatgcctg ttc                                          23

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
cggccgcaca cgtcctcc                                                18

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cggccgcgca cgtcctcctc                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cactgccagg cacttctgca                                              20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
cactgccagg cgcttctgca g                                            21

<210> SEQ ID NO 10
<211> LENGTH: 17
<212> TYPE: DNA
```

-continued

```
<213> ORGANISM: Artificial Sequence
<220> FEATURE:
<223> OTHER INFORMATION: Primer

<400> SEQUENCE: 10
acgcgggcac ggctgtc                                                  17

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
ctcgcggatg gcgctga                                                  17
```